(12) United States Patent
Dunn et al.

(10) Patent No.: US 11,998,437 B2
(45) Date of Patent: Jun. 4, 2024

(54) METHODS FOR LENGTHENING TUBULAR ORGANS

(71) Applicant: THE BOARD OF TRUSTEES OF THE LELAND STANFORD JUNIOR UNIVERSITY, Stanford, CA (US)

(72) Inventors: James C. Y. Dunn, Palo Alto, CA (US); Thomas M. Krummel, Los Altos Hills, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 206 days.

(21) Appl. No.: 17/321,277

(22) Filed: May 14, 2021

(65) Prior Publication Data

US 2022/0061977 A1 Mar. 3, 2022

Related U.S. Application Data

(60) Provisional application No. 63/070,040, filed on Aug. 25, 2020.

(51) Int. Cl.
*A61F 2/04* (2013.01)

(52) U.S. Cl.
CPC .......... *A61F 2/04* (2013.01); *A61F 2002/045* (2013.01); *A61F 2210/0057* (2013.01); *A61F 2220/0008* (2013.01); *A61F 2230/0091* (2013.01); *A61F 2250/0007* (2013.01); *A61F 2250/0059* (2013.01)

(58) Field of Classification Search
CPC .................. A61F 2/04; A61F 2002/045; A61F 2210/0057; A61F 2220/0008; A61F 2230/0091; A61F 2250/0007; A61F 2250/0059
See application file for complete search history.

(56) References Cited

U.S. PATENT DOCUMENTS

2012/0083820 A1* 4/2012 Carman ..................... A61F 2/88
606/191
2020/0368007 A1* 11/2020 Abdelmoaty .......... A61B 34/73

OTHER PUBLICATIONS

Dubrovsky et al (Journal of Pediatric Surgery "Intestinal lengthening via multiple in-continuity springs"; vol. 54, Issue 1, Jan. 2019, pp. 39-43) (Year: 2019).*

* cited by examiner

*Primary Examiner* — Brian A Dukert
*Assistant Examiner* — Rebecca Lynee Zimmerman
(74) *Attorney, Agent, or Firm* — Rimon PC

(57) ABSTRACT

Described herein are methods for lengthening tubular organs using expandable implants. The expandable implants may be secured along a length of a tubular organ by forming a plication at each end of the implant. Securing the expandable implants in this manner may be used to treat short bowel syndrome. Methods for selecting and implanting an expandable implant suitable for lengthening a tubular organ according to predetermined patient parameters are further described herein.

8 Claims, 15 Drawing Sheets

FIG. 2

| Wall Thickness (mm) \ R_out (cm) | 0.5 | 0.75 | 1 | 1.25 | 1.5 | 1.75 | 2 | 2.25 | 2.5 | 2.75 | 3 |
|---|---|---|---|---|---|---|---|---|---|---|---|
| 0.25 | | | | | | 0.657 | 1.12 | 1.234 | 1.45 | 1.57 | 1.87 |
| 0.5 | | | | | 1.11 | 1.313 | 1.57 | 1.689 | 1.98 | 2.26 | 2.51 |
| 0.6 | | | | 1.111 | 1.28 | 1.603 | 1.77 | 2.163 | 2.35 | 2.61 | 3.03 |
| 0.7 | | | 0.959 | 1.286 | 1.55 | 1.806 | 2.21 | 2.421 | 2.84 | 3.06 | 3.44 |
| 0.8 | | | 1.215 | 1.447 | 1.8 | 2.074 | 2.49 | 2.8 | 3.11 | 3.46 | 3.91 |
| 0.9 | | | 1.289 | 1.717 | 1.94 | 2.342 | 2.73 | 3.086 | 3.47 | 3.95 | 4.37 |
| 1 | | 1.104 | 1.508 | 1.849 | 2.23 | 2.69 | 3.09 | 3.479 | 3.86 | 4.34 | 4.84 |
| 1.1 | | 1.23 | 1.642 | 2.077 | 2.49 | 2.846 | 3.4 | 3.864 | 4.27 | 4.74 | 5.25 |
| 1.2 | | 1.28 | 1.684 | 2.307 | 2.72 | 3.261 | 3.76 | 4.201 | 4.73 | 5.21 | 5.78 |
| 1.3 | | 1.368 | 1.851 | 2.415 | 3.01 | 3.5 | 3.94 | 4.584 | 5.15 | 5.58 | 6.17 |
| 1.4 | | 1.567 | 2.027 | 2.607 | 3.11 | 3.654 | 4.3 | 4.812 | 5.49 | 6.13 | 6.74 |
| 1.5 | | 1.708 | 2.152 | 2.732 | 3.37 | 4.07 | 4.59 | 5.161 | 5.82 | 6.55 | 7.19 |
| 1.6 | | 1.837 | 2.412 | 2.995 | 3.67 | 4.234 | 4.97 | 5.62 | 6.26 | 6.94 | 7.59 |
| 1.7 | 1.27 | 1.884 | 2.46 | 3.25 | 3.88 | 4.603 | 5.18 | 5.864 | 6.61 | 7.37 | 8.07 |
| 1.8 | 1.38 | 2.025 | 2.617 | 3.391 | 4.05 | 4.803 | 5.53 | 6.244 | 6.98 | 7.81 | 8.54 |
| 1.9 | 1.46 | 2.037 | 2.773 | 3.631 | 4.28 | 5.039 | 5.8 | 6.594 | 7.32 | 8.21 | 9.03 |
| 2 | 1.52 | 2.306 | 2.997 | 3.831 | 4.5 | 5.299 | 6.19 | 6.912 | 7.72 | 8.63 | 9.45 |
| 2.1 | 1.63 | 2.396 | 3.118 | 3.895 | 4.75 | 5.557 | 6.42 | 7.267 | 8.16 | 9 | 9.86 |
| 2.2 | 1.82 | 2.506 | 3.329 | 4.097 | 4.97 | 5.893 | 6.78 | 7.689 | 8.47 | 9.36 | 10.4 |
| 2.3 | 1.68 | 2.624 | 3.503 | 4.314 | 5.3 | 6.172 | 7.1 | 7.947 | 8.96 | 9.89 | 10.8 |
| 2.4 | 1.71 | 2.638 | 3.647 | 4.604 | 5.48 | 6.331 | 7.41 | 8.295 | 9.22 | 10.2 | 11.2 |
| 2.5 | 1.89 | 2.757 | 3.713 | 4.744 | 5.73 | 6.689 | 7.65 | 8.651 | 9.69 | 10.7 | 11.7 |
| 2.6 | 1.98 | 2.864 | 3.916 | 4.925 | 5.86 | 6.99 | 8.03 | 9.031 | 10.1 | 11.1 | 12.1 |
| 2.7 | 2.04 | 2.994 | 4.113 | 5.05 | 6.11 | 7.252 | 8.2 | 9.374 | 10.4 | 11.5 | |
| 2.8 | 2.03 | 3.079 | 4.151 | 5.319 | 6.46 | 7.534 | 8.63 | 9.687 | 10.9 | 12 | |
| 2.9 | 2.19 | 3.244 | 4.421 | 5.55 | 6.6 | 7.757 | 8.95 | 10.07 | 11.3 | | |
| 3 | 2.29 | 3.397 | 4.58 | 5.622 | 6.88 | 7.98 | 9.15 | 10.39 | 11.6 | | |

*FIG. 3*

METHODS FOR LENGTHENING TUBULAR ORGANS

CROSS-REFERENCE TO RELATED APPLICATIONS

This application claims priority to U.S. Provisional Patent Application Ser. No. 60/070,040, filed Aug. 25, 2020, which is incorporated herein by reference.

TECHNICAL FIELD

This application describes methods for lengthening tubular organs using expandable implants. The expandable implants may be springs that are secured along a length of a tubular organ by forming a plication at each end of the spring. Securing the expandable implants in this manner may be used to treat short bowel syndrome. Methods for selecting an expandable implant suitable for lengthening a tubular organ according to predetermined patient parameters are also described herein.

BACKGROUND

Short bowel syndrome (SBS), also known as short gut syndrome, occurs in patients with insufficient length of intestine to maintain normal digestion and absorption. SBS is a condition associated with malnutrition, malabsorption, and dehydration due to loss of large amounts of intestinal tissue. The most common causes of SBS in the pediatric population are necrotizing enterocolitis, intestinal atresias, volvulus, and abdominal wall defects.

Medical treatment for SBS includes administration of parenteral nutrition to provide necessary nutrients and hydration. Surgical treatment options for SBS include intestinal transplantation, procedures that taper and lengthen the intestine to increase absorption area, and procedures that slow down transit time, for example, colon interposition and the creation of recirculating loops. However, these procedures have had limited success and are often associated with significant complications. Hyperalimentation via the parenteral route remains the mainstay of treatment, but is associated with complications such as catheter related infections, liver failure, and osteoporosis.

Recently, the concept of using mechanical force to lengthen intestinal tissue has been studied using a variety of tissue expander devices. Several methods of applying mechanical force to an intestinal segment have been developed, including repeated injections of saline solution, gradual advancement of a screw, and use of a hydraulic piston. However, many of these methods require repeated interventions such as serial screw advancements or saline injections. Additionally, all of these techniques incorporate a device that is at least partly outside the abdominal cavity, which introduces risks such as dislodgement, damage to the exterior component, infection, and fistula formation.

Techniques for distraction enterogenesis, where axial force is applied by springs implanted in the small bowel, have also been employed to create increased intestinal length. These springs were either sutured to the intestinal wall or secured thereto by anchoring structures such as hooks, barbs, studs, etc. Accordingly, it would be beneficial to have alternative methods that temporarily secure or contain the intestinal implants within the small bowel and other tubular organs. Furthermore, given that excessive mechanical force may cause life-threatening complications such as intestinal perforation, it would be useful to have methods for selecting devices that provide the appropriate amount of force for the amount of lengthening desired in a tubular organ of a patient.

SUMMARY

Described herein are methods for lengthening tubular organs using expandable implants, for example, using expandable springs. The expandable implants may be secured along a length of a tubular organ by forming a plication at each end of the implant. Plications may be created by folding tissue and then suturing the tissue together so that the folded configuration is maintained. When secured in the small intestine in this manner, the expandable implants may be used to treat short bowel syndrome (SBS). Methods for selecting an expandable implant suitable for providing an appropriate amount of force for the amount of lengthening desired in a tubular organ are also described herein.

In general, the methods for lengthening a segment of an elongate tubular organ include: placing one or more axially expanding implants into a lumen of the elongate tubular organ at a target location, the lumen having a diameter, and the one or more implants having a proximal end, a distal end, an expanded configuration, and a compressed configuration; forming a plication in the elongate tubular organ adjacent to the proximal and distal ends of each implant to temporarily secure each implant within the elongate tubular organ, where the plication at the proximal and distal ends of each implant reduces the diameter of the lumen by about 20% to about 80% of its original diameter without the plication; and applying a force on the target location using the one or more axially expanding implants to lengthen the segment of the elongate tubular organ.

These methods may be used to treat various tubular organs, for example, the small intestine, the large intestine, ureter, etc. The axially expanding implant may be placed into the lumen of the elongate tubular organ at a target location in the compressed configuration between two plications, and then expanded at the target location over a period of time. Expansion of the axially expanding implant applies a force on a segment of the elongate tubular organ that may result in lengthening of that segment, and in turn, the tubular organ. After lengthening, the implants may naturally pass out of the tubular organ. The methods may be beneficial in treating short bowel syndrome.

Methods for lengthening a segment of an elongate tubular organ are provided herein in frequent embodiments. Such methods include placing one or more axially expanding implants into a lumen of the elongate tubular organ at a target location, the lumen having a diameter, and the one or more implants having a proximal end, a distal end, an expanded configuration, and a compressed configuration; forming a plication in the elongate tubular organ adjacent to the proximal and distal ends of each implant to temporarily secure each implant within the elongate tubular organ, wherein the plication at the proximal and distal ends of each implant reduces the diameter of the lumen by about 20% to about 80%; and applying a force on the target location using the one or more axially expanding implants to lengthen the segment of the elongate tubular organ. Also often, the one or more axially expanding implants are placed into the lumen of the elongate tubular organ in the compressed configuration and then expanded at the target location over a period time. Frequently, the period of time ranges from about one week to about three weeks. The tubular organ is often the small intestine or another tubular organ. Often the method is adapted for treating short bowel syndrome in a subject.

Methods of selecting or making an expandable implant for lengthening a segment of an elongate tubular organ in a subject are also provided, such methods often involve determining a parameter related to the elongate tubular organ of the subject at a target location, wherein the parameter is selected from one or more of weight of the subject, height of the subject, age of the subject, a radius of the elongate tubular organ of the subject at the target location, a diameter of the elongate tubular organ at the target location, and a wall thickness of the elongate tubular organ at the target location; determining a target amount of force capable of lengthening the elongate tubular organ at the target location; and selecting and making the expandable implant having one or more characteristics capable of producing the target amount of force. Frequently, the methods further include implanting the selected or made expandable implant into the target location of the elongate tubular organ.

According to frequent embodiments, two or more expandable implants are selected or made, the method comprising: determining a parameter related to the elongate tubular organ of the subject at two or more target locations, wherein the parameter is selected from one or more of weight of the subject, height of the subject, age of the subject, a radius of the elongate tubular organ of the subject at the two or more target locations, a diameter of the elongate tubular organ at the two or more target locations, and a wall thickness of the elongate tubular organ at the two or more target locations; determining a target amount of force capable of lengthening the elongate tubular organ at the two or more target locations; and selecting and making the two or more expandable implants, each having one or more characteristics capable of producing the target amount of force. Often the methods include implanting the two or more expandable implants at the two or more target locations.

Often, the expandable implant has a proximal end, a distal end, an expanded configuration, and a compressed configuration, and wherein the implanting comprises forming a plication in the elongate tubular organ adjacent to the proximal end and the distal end of the expandable implant when present in the elongate tubular organ at the target location in the compressed configuration. Also often, the determining step comprises at least two parameters comprising the radius of the elongate tubular organ of the subject at the target location and the wall thickness of the elongate tubular organ at the target location. According to frequent embodiments, the expandable implant comprises a self-expanding spring, and the one or more expandable implant characteristics are selected from one or more of the group consisting of spring diameter, uncompressed spring length, number of spring turns, and spring constant.

In frequent embodiments, the plication at the proximal and distal ends of each implant reduces the diameter of the lumen by about 50%. Also often, the plication at the proximal and distal ends of each implant reduces the diameter of the lumen by about 25% of its original diameter. Also often, the plication at the proximal and distal ends of each implant reduces the diameter of the lumen by about 30% of its original diameter. Also often, the plication at the proximal and distal ends of each implant reduces the diameter of the lumen by about 35% of its original diameter. Also often, the plication at the proximal and distal ends of each implant reduces the diameter of the lumen by about 40% of its original diameter. Also often, the plication at the proximal and distal ends of each implant reduces the diameter of the lumen by about 45% of its original diameter. Also often, the plication at the proximal and distal ends of each implant reduces the diameter of the lumen by about 50%. Also often, the plication at the proximal and distal ends of each implant reduces the diameter of the lumen by about 55% of its original diameter. Also often, the plication at the proximal and distal ends of each implant reduces the diameter of the lumen by about 60% of its original diameter. Also often, the plication at the proximal and distal ends of each implant reduces the diameter of the lumen by about 65% of its original diameter. Also often, the plication at the proximal and distal ends of each implant reduces the diameter of the lumen by about 70% of its original diameter. Also often, the plication at the proximal and distal ends of each implant reduces the diameter of the lumen by about 75% of its original diameter. Also often, the plication at the proximal and distal ends of each implant reduces the diameter of the lumen between about 40% to 70% of its original diameter. Also often, the plication at the proximal and distal ends of each implant reduces the diameter of the lumen between about 35% to 60% of its original diameter.

Also frequently, the applied force increases the length of the segment at least two-fold. Often, the applied force increases the length of the segment at least 2.5-fold. Also often, the applied force increases the length of the segment between two-fold and at least 2.5-fold.

Often, two or more axially expanding implants are placed (concurrently or successively) into the lumen of the elongate tubular organ. Also often, three or more axially expanding implants are concurrently placed into the lumen of the elongate tubular organ.

In frequent embodiments, the implant has a length ranging from about 5 cm to about 8 cm in the expanded configuration. Often, the implant has a length of about 7.5 cm in the expanded configuration. Also often, the implant has a length ranging from about 4 cm to about 10 cm in the expanded configuration. Frequently, the implant has a length ranging from about 0.5 cm to about 2.0 cm in the compressed configuration.

According to often included embodiments, the plication is formed using a non-absorbable suture. Frequently, the plication is formed using an absorbable suture.

Also according to often included embodiments, the one or more axially expanding implants comprise a hollow tubular body that maintains patency of the lumen and passage of bodily contents therethrough. For example, the one or more axially expanding implants frequently comprise a spring made from a metal, a polymeric material, or nickel-titanium alloy (Nitinol).

According to often included embodiments, the one or more axially expanding implants comprises an anchoring member.

According to often included embodiments, at least a portion of the one or more axially expanding implants comprises a protective covering. Often the protective covering is disposed on the proximal and distal ends of the one or more axially expanding implants.

Frequently, the one or more axially expanding implants comprises a dissolvable or dispersible coating. Often such dissolvable or dispersible coating is adapted to hold the one or more axially expanding implants in a compressed configuration prior to implantation. The dissolvable or dispersible coating is frequently adapted to dissolve or disperse under physiological conditions, such as those found in the small intestine, the large intestine, or another tubular organ. In certain embodiments, the dissolvable or dispersible coating comprises cellulose acetate phthalate or another polymer phthalate. Often the dissolvable or dispersible coating is an enteric coating.

According to frequent embodiments, the one or more axially expanding implants comprises a spring having a spring constant of at least 1.6 N/m. Often, the one or more axially expanding implants comprises a spring having a spring constant ranging from about 5 N/m to about 50 N/m. Also often, the one or more axially expanding implants comprises a spring having a spring constant ranging from about 1.6 N/m to about 50 N/m. Also often, the one or more axially expanding implants comprises a spring having a spring constant ranging from about 2 N/m to about 45 N/m. Also often, the one or more axially expanding implants comprises a spring having a spring constant ranging from about 2 N/m to about 40 N/m. Also often, the one or more axially expanding implants comprises a spring having a spring constant ranging from about 2 N/m to about 35 N/m. Also often, the one or more axially expanding implants comprises a spring having a spring constant ranging from about 2 N/m to about 30 N/m. Also often, the one or more axially expanding implants comprises a spring having a spring constant ranging from about 2 N/m to about 25 N/m. Also often, the one or more axially expanding implants comprises a spring having a spring constant ranging from about 2 N/m to about 20 N/m. Also often, the one or more axially expanding implants comprises a spring having a spring constant ranging from about 2 N/m to about 15 N/m. Also often, the one or more axially expanding implants comprises a spring having a spring constant ranging from about 2 N/m to about 10 N/m.

Also, according to frequently included embodiments, the one or more axially expanding implants is placed laparoscopically or via an open surgical procedure.

According to frequently included embodiments, the one or more axially expanding implants is selected based on a thickness of a wall of the elongate tubular organ at the target location, a radius of the elongate tubular organ at the target location, and/or a diameter of the elongate tubular organ at the target location.

In frequent embodiments, the subject is a pediatric patient. Often, the subject is an adult patient.

Methods for selecting an expandable implant for lengthening a segment of an elongate tubular organ in a patient are further described herein. In general, the methods include: generating a first modeling platform based upon a first set of experimental parameters; translating the first modeling platform to generate a second modeling platform, the second modeling platform being based upon at least two patient parameters; using the second modeling platform to determine a target amount of force capable of lengthening the elongate tubular organ; selecting the expandable implant having one or more characteristics capable of producing the target amount of force; and implanting the selected expandable implant into a target segment of the elongate tubular organ. The target amount of force may range from about 0.3 N to about 0.8 N. The expandable implant may be a self-expanding spring.

All patents, patent applications, and publications mentioned herein, both supra and infra, are hereby incorporated by reference in their entireties.

BRIEF DESCRIPTION OF THE DRAWINGS

The skilled person in the art will understand that the drawings, described below, are for illustration purposes only. The drawings are incorporated in and constitute a part of this specification.

FIG. 2 is an animal force table (first modeling platform) obtained using the experimental parameters of small intestinal wall thickness and radius of pigs.

FIG. 3 is a human force table (second modeling platform) obtained by translating the values presented in FIG. 2 based on the patient characteristics of small intestinal wall thickness and radius.

DETAILED DESCRIPTION

Figure 1:
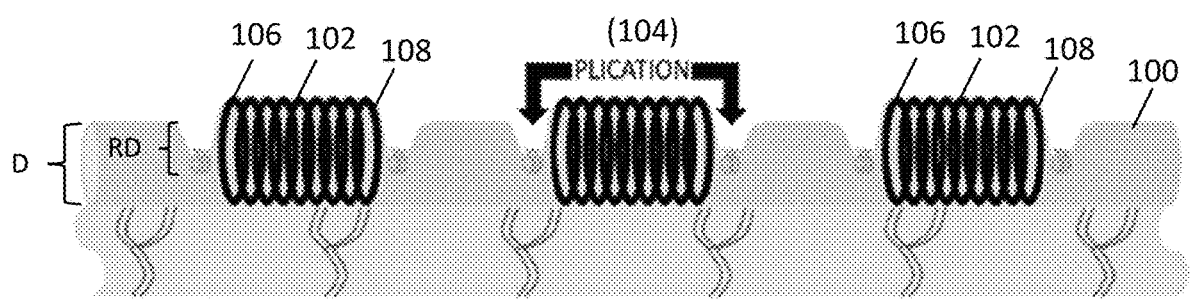
FIG. 1 is a schematic representation of a portion of small intestine in cross-section showing the location of plications relative to three exemplary expandable springs.

For clarity of disclosure, and not by way of limitation, the detailed description of the various embodiments is provided into certain subsections that follow. A single embodiment may be discussed in multiple subsections.

Unless otherwise defined herein, scientific and technical terms used in connection with the present application shall have the meanings that are commonly understood by those of ordinary skill in the art to which this disclosure belongs. This disclosure is not limited to the particular methodology, protocols, and reagents, etc., described herein and as such can vary. The terminology used herein is for the purpose of describing particular embodiments only and is not intended to limit the scope of the present invention, which is defined solely by the claims. Definitions of common terms in immunology, and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

As used herein, "treatment" means any way the symptoms of a condition, disorder or disease are ameliorated or otherwise beneficially altered.

As used herein, "subject" often refers to an animal, including, but not limited to, a primate (e.g., human). The terms "subject" and "patient" are used interchangeably herein.

As described herein, to deliver a safe and efficient outcome for distraction enterogenesis using a self-expanding intraluminal implant, applied mechanical force of the implant is scaled based on intestinal size to ensure the delivered physical force is customizable based on the physical characteristics of small intestine for each subject. Such scaling provides for lengthening while minimizing the risk of tissue injury. As described, data from human tissues is provided to evaluate the range of changes in geometrical characteristics (thickness and diameter) of the small intestine in human patients. Mechanical characterization of the intestinal tissue was also conducted, and the findings are incorporated in computational models described herein. Exemplary models and methods provided herein are adapted for use in human subjects and non-human subjects for lengthening a segment of an elongate tubular organ.

Described herein are methods for lengthening tubular organs using expandable implants. The expandable implants may be secured along a length of a tubular organ by forming a plication at each end of the implant. Plications may be created by folding tissue and then suturing the tissue together so that the folded configuration is maintained for a period of time, and in a manner that temporarily holds or contains the expandable implant at a target location in the tubular organ to effect lengthening at the target location. Further described herein are methods for selecting an expandable implant suitable for lengthening a tubular organ according to predetermined patient parameters.

Elongate tubular organs may be lengthened by placing one or more axially expanding implants into a lumen of the tubular organ or segments thereof. The number of implants placed in the elongate tubular organ may depend on such factors as the organ of implantation, the desired amount of lengthening, and the type of implant being employed. Between one and five axially expanding implants are generally implanted. For example, one expanding implant, two expanding implants, three expanding implants, four expanding implants, or five expanding implants may be placed at a target location in an elongate tubular organ. In one variation, at least three axially expanding implants are placed in an elongate tubular organ. In other variations, more than 5 axially expanding implants are placed in an elongate tubular organ. In further variations, multiple axially expanding implants are placed adjacent to each other in series. In some variations, multiple axially expanding implants are spaced or distributed evenly or unevenly within the elongate tubular organ. Placement of the implants may be via laparoscopy, or by an open surgical procedure. The elongate tubular organ may be the small intestine, large intestine, ureter, etc.

The expandable implants generally include a proximal end, a distal end, an expanded configuration, and a compressed configuration. Although typically axially expandable, the implants may also expand in the radial direction. In some variations, the axially expanding implants are self-expanding. To effect lengthening, the axially expanding implants are placed in the lumen of an elongate tubular organ in the compressed configuration, and then allowed to gradually expand over a period of time. The period of time may range from about one week to about 8 weeks, or from about one week to about three weeks. For example, the period of time may be about one week, about two weeks, about three weeks, about four weeks, about five weeks, about six weeks, about seven weeks, or about eight weeks.

The axially expanding implants generally include a hollow tubular body that maintains patency of the lumen of the elongate organ so that bodily contents, for example, digested food and/or bodily fluids, may pass therethrough. The axially expanding implants may be structured as hollow tubes, coils, or springs. They may also be formed as braided or woven stent-like structures from filaments or wires. With respect to material composition, the axially expanding implants may be made from any suitable material, for example, a metal, nickel-titanium alloy (Nitinol), or a biodegradable or non-biodegradable polymer.

Exemplary biodegradable polymers include without limitation, polyarylates (L-tyrosine-derived or free acid), poly (α-hydroxy-esters), poly(β-hydroxy-esters), polyamides, poly(amino acid), polyalkanotes, polyalkylene alkylates, polyalkylene oxylates, polyalkylene succinates, polyanhydrides, polyanhydride esters, polyaspartimic acid, polybutylene diglycolate, poly(caprolactone), poly(caprolactone)/ poly(ethylene glycol) copolymers, poly(carbonate), L-tyrosine-derived polycarbonates, polycyanoacrylates, polydihidropyrans, poly(dioxanone), poly-p-dioxanone, poly(epsilon-caprolactone), poly(epsilon-caprolactone-dimethyltrimethylene carbonate), poly(esteramide), poly(esters), aliphatic polyesters, poly(etherester), poly(ethylene glycol)/poly(orthoester) copolymers, poly(glutarunic acid), poly(glycolic acid), poly(glycolide), poly(glycolide)/poly(ethylene glycol) copolymers, poly(glycolide-trimethylene carbonate), poly(hydroxyalkanoates), poly(hydroxybutyrate), poly(hydroxybutyrate-co-valerate), poly(imino carbonates), polyketals, poly(lactic acid), poly(lactic acid-co-glycolic acid), poly(lactic acid-co-glycolic acid)/poly(ethylene glycol) copolymers, poly(lactide), poly(lactide-co-caprolactone), poly(DL-lactide-co-glycolide), poly(lactide-co-glycolide)/poly(ethylene glycol) copolymers, poly(lactide)/poly(ethylene glycol) copolymers, poly(lactide)/poly(glycolide) copolymers, polyorthoesters, poly(oxyethylene)/poly(oxypropylene) copolymers, polypeptides, polyphosphazenes, polyphosphoesters, polyphosphoester urethanes, poly(propylene fumarate-co-ethylene glycol), poly(trimethylene carbonate), polytyrosine carbonate, polyurethane, PorLastin or silk-ealastin polymers, spider silk, tephaflex, terpolymer (copolymers of glycolide, lactide or dimethyltrimethylene carbonate), and combinations, mixtures or copolymers thereof. In one variation, the biodegradable polymer is polycaprolactone (PCL).

Examples of non-biodegradable polymers suitable to make the axially expanding implants described herein include, but are not limited to, poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

The implants are typically formed as self-expanding structures. When configured as a spring, the spring may be capable of multi-fold (e.g., 5-10 times) expansion from a compressed state. The spring may include a plurality of coils wound to have a diameter sized to substantially match the internal diameter of the lumen of the elongate tubular organ. The gauge, pitch, and diameter of the spring may be sized to vary the force applied by it. For example, the spring may have a diameter sized for optimal engagement with the internal walls of the lumen while in its expanded form. To achieve the appropriate distension force, the gauge and/or pitch of the spring may be increased to increase the force applied by a spring of a set diameter. Spring diameters may range from about 0.5 cm to about 6 cm (radius of 0.25 cm to about 3 cm). For example, the spring diameter may be about 0.5 cm, about 1.0 cm, about 1.5 cm, about 2.0 cm, about 2.5 cm, about 3.0 cm, about 3.5 cm, about 4 cm, about 4.5 cm, about 5 cm, about 5.5 cm, or about 6 cm.

The fully expanded length of the axially expanding implant, e.g., a spring, may also be configured to provide the desired level of distension of the organ upon expansion. Implant lengths in the expanded configuration may range from about 2 cm to about 8 cm, or from about 5 cm to about 8 cm. For example, the implant length in the expanded configuration may be about 2 cm, about 3 cm, about 4 cm, about 5 cm, about 6 cm, about 7 cm, or about 8 cm. In some variations, the implant may have a length greater than 8 cm in the expanded configuration.

When configured as a spring, the axially expanding implant generally has a spring constant ranging from about 1.6 N/m to about 50 N/m, or from about 5 N/m to about 50 N/m. For example, the spring constant may be about 1.6 N/m, about 5 N/m, about 10 N/m, about 15 N/m, about 20 N/m, about 25 N/m, about 30 N/m, about 35 N/m, about 40 N/m, about 45 N/m, or about 50 N/m.

In some variations, the axially expanding implants comprise an anchoring member to aid in securing it to the lumen of the elongate tubular organ. One or more anchoring members may be provided on the implant, in any suitable configuration that helps secure or hold it within the elongate tubular organ. For example, the anchoring members may be disposed on the ends of the implant, symmetrically or asymmetrically spaced upon the implant, patterned on the implant, etc. Exemplary anchoring members include without limitation, hooks, barbs, and stubs. The anchoring members made be formed from biodegradable or non-biodegradable materials.

In one variation, the axially expanding implant comprises a spring having a covering or cap on its proximal and distal ends. The covering or cap may be made from a polymer such as silicone, and may protect tissue from catching on the ends of the spring and being injured, in addition to providing a larger diameter at the ends of the spring to improve the friction fit of the spring against the wall of the tubular organ. In other variations, the spring may be provided in a capsule for protecting tissue from spring ends. The capsule would dissolve after placement in the tubular organ. For example, the spring may be placed within a gelatin capsule prior to implantation within the small intestine.

One or more axially expanding implants, as described herein, may be placed in the lumen of an elongate tubular organ to lengthen the tubular organ. The axially expanding implants are generally held in place at a target location in the tubular organ for a period of time that results in lengthening of the tubular organ. The period of time may range from about one week to about 8 weeks, or from about one week to about three weeks. For example, the period of time may be about one week, about two weeks, about three weeks, about four weeks, about five weeks, about six weeks, about seven weeks, or about eight weeks.

In some variations, plications are used to temporarily hold one or more axially expanding implants at the target location within the elongate tubular organ lumen. Plications may be formed by folding tissue of the tubular organ and then suturing the tissue together to maintain the folded configuration. When created in the small intestine or other elongate tubular organs, plications reduce the lumen diameter so that the axially expanding implants are contained between the plications and their transit through the tubular organ prevented until the plication is relaxed or released.

For example, referring to FIG. 1, the small intestine (100) is shown with three axially expanding implants (102) contained within its lumen. Plications (104) that have been formed by sutures at the proximal ends (106) and distal ends (108) of the axially expanding springs (102) reduce the diameter of the small intestine (100) from (D) to (RD). The amount of reduction in lumen diameter may range from about 20% to about 80%. For example, the reduction may be about 20%, about 30%, about 40%, about 50%, about 60%, about 70%, or about 80%. In some variations, the reduction in lumen diameter may be about 50%. Absorbable or non-absorbable sutures may be used to create the plications. In some variations, non-absorbable sutures are employed so that the implants can pass out of the tubular organ without surgery after lengthening.

The methods described herein may be used to treat various tubular organs, for example, the small intestine, the large intestine, ureter, etc. The axially expanding implant may be placed into the lumen of the elongate tubular organ at a target location in the compressed configuration between two plications, and then expanded at the target location over a period of time, for example, between about one week and about three weeks. Expansion of the axially expanding implant applies a force on a segment of the elongate tubular organ that may result in lengthening of that segment, and in turn, the tubular organ. The methods may be beneficial for use in the small intestine and for treating short bowel syndrome.

While temporarily held within the elongate tubular organ, the axially expanding implants apply an axial force to a segment of the elongate tubular organ that generally increases the length of the tubular organ segment. In some variations, the applied force increases the length of the segment at least two-fold. In other variations, the applied force increases the length of the segment at least 2.5-fold. Varying or adjusting the degree of plication (e.g., the amount of reduction in lumen diameter) may optimize the amount of small intestinal lengthening using a Nitinol spring, as further detailed in the animal study presented in Example 1.

In brief, the study in Example 1 showed that plication resulting in a 50% reduction in lumen diameter yields the greatest lengthening. Additionally, the study illustrated that using dissolvable (biodegradable) sutures may still achieve lengthening while ultimately allowing springs to be naturally excreted from the intestine, thus avoiding a second operation for spring retrieval. In examining the histology, it was noted that all lengthened segments had significant increases in crypt depth and muscularis propria thickness. This finding corroborates previous studies that demonstrated similar changes at the cellular level, and supports the idea that there is indeed new tissue growth and not simply thinning of existing tissue.

The study in Example 1 also showed that lesser degrees of plication, e.g., plication that reduced lumen diameter by less than 50%, may jeopardize the success of lengthening as the spring was not well secured. Some evidence from the study showed that plication of less than 50% compromised lengthening because both a 10% and a 30% plication resulted in a decreased amount of lengthening. Review of the radiologic data provided an indication as to why this happened, illustrating that with these lesser degrees of plication, the springs expanded more quickly in the first week post-operatively, suggesting that they were not well secured and that they were able to partially slip past the plication sutures. However, at 50% plication, significant lengthening was achieved (2.7-fold increase in intestine segment length) while avoiding the complications of intestinal obstruction. Greater degrees of plication may have a higher risk of this complication, and likely without adding significantly to lengthening.

In a second set of experiments described further in Example 1, a 50% plication was employed, but dissolvable (biodegradable) sutures instead of non-biodegradable sutures were used. The pigs were able to be advanced to regular diets at three weeks even with springs still in their original positions as confirmed by radiographs. It is important to note that this did not result in any obstructive symptoms, and also did not cause the springs to immediately pass out of the intestine, which typically been shown to occur after about two months. This speaks to the ability of gastrointestinal contents to safely pass through the implanted springs. The ability of the springs to naturally pass out of the intestine weeks after lengthening may be a significant finding, as it obviates the need for re-operation to remove the springs once lengthening is complete. A significant challenge in spring-mediated intestinal lengthening is the need for surgery to implant and explant the springs, since each new operation would carry risks for patients, and may even require the resection of much-needed bowel.

Overall, the study presented in Example 1 demonstrated that a 50% reduction in intestinal diameter may be optimal in both securing springs for intestinal lengthening while also avoiding symptoms of intestinal obstruction. Dissolvable sutures may be used to achieve intestinal lengthening, and at two months post-operatively, this allows for the natural expulsion of the springs out of the animal, which avoids a second operation for spring retrieval. These optimizations of spring-mediated lengthening offer improved strategies for developing potential therapies for SBS.

The modeling methods described herein may be used to select an axially expanding implant suitable for providing an appropriate amount of force for the amount of lengthening desired in a tubular organ when distraction enterogenesis is being performed. Selection according to these methods may help to avoid complications such as intestinal perforation and optimize the lengthening process. The methods translate animal parameters to human/patient parameters using computational methods, and generate a force table (second modeling platform) that allows selection of an implant, e.g., a spring, capable of producing the desired amount of force identified from the table.

In general, the methods include: generating a first modeling platform based upon a first set of experimental parameters; translating the first modeling platform to generate a second modeling platform, the second modeling platform being based upon at least two patient parameters; using the second modeling platform to determine a target amount of force capable of lengthening the elongate tubular organ; and selecting the expandable implant having one or more characteristics capable of producing the target amount of force. The target amount of force may range from about 0.3 N to about 0.8 N. The expandable implant may be a self-expanding spring. Furthermore, the patient may be an adult or pediatric patient.

Figure 2:
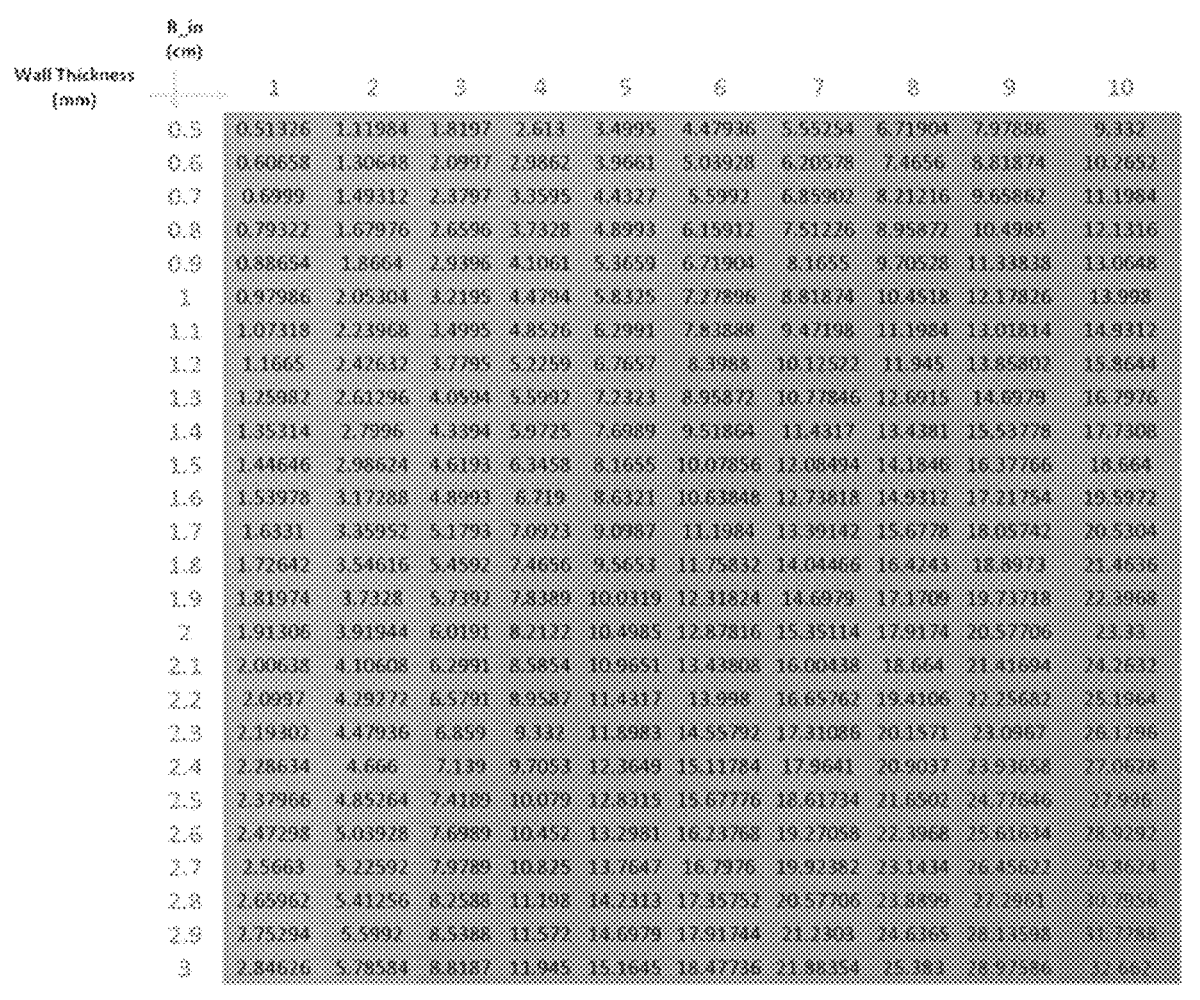

The first modeling platform may be generated based on a first set of experimental parameters. Experimental parameters are generally obtained from animals, e.g., from pigs or mice. Exemplary experimental parameters include without limitation, a radius of the elongate tubular organ, a diameter of the elongate tubular organ, and a wall thickness of the elongate tubular organ. These experimental parameters may be used to calculate a target amount of force for tubular organ lengthening. For example, referring to FIG. 2, a first modeling platform (table) is shown with target force values calculated from experimental parameters of radius of the elongate tubular organ and wall thickness of the elongate tubular organ.

Next, the first modeling platform may be translated to generate a second modeling platform, where the second modeling platform is based upon at least two patient parameters. The first and second modeling platforms may be generated using computational methods run on the commercially available finite-element software ABAQUS (version 2017, SIMULIA, Providence, RI) using implicit solver. Exemplary patient parameters include without limitation, weight, height, age, radius of the elongate tubular organ of the patient, diameter of the elongate tubular organ of the patient, and wall thickness of the elongate tubular organ of the patient. Referring to FIG. 3, a second modeling platform (table) is shown with target force values calculated from patient parameters of radius of the elongate tubular organ and wall thickness of the elongate tubular organ.

Once the target force value is obtained, a suitable implant may be selected that would be capable of producing that amount of force in the elongate tubular organ. The selected implant may then be placed into a target segment of an elongate tubular organ. Here, one or more implant characteristics may be used to determine whether an implant can provide the necessary amount of force. For example, when the axially expandable implant is a self-expanding spring, the one or more implant characteristics may be spring diameter, uncompressed spring length, number of spring turns (e.g., pitch), or spring constant. The uncompressed spring length may range from about 2 cm to about 8 cm, or from about 5 cm to about 8 cm. For example, the uncompressed spring length may be about 2 cm, about 3 cm, about 4 cm, about 5 cm, about 6 cm, about 7 cm, or about 8 cm. In some variations, the uncompressed spring may have a length greater than 8 cm. Spring diameters may range from about 0.5 cm to about 6 cm (radius of 0.25 cm to about 3 cm). For example, the spring diameter may be about 0.5 cm, about 1.0 cm, about 1.5 cm, about 2.0 cm, about 2.5 cm, about 3.0 cm, about 3.5 cm, about 4 cm, about 4.5 cm, about 5 cm, about 5.5 cm, or about 6 cm.

Furthermore, when configured as a spring, the axially expanding implant may generally have a spring constant ranging from about 1.6 N/m to about 50 N/m, or from about 5 N/m to about 50 N/m. For example, the spring constant may be about 1.6 N/m. about 5 N/m, about 10 N/m, about 15 N/m, about 20 N/m, about 25 N/m, about 30 N/m, about 35 N/m, about 40 N/m, about 45 N/m, or about 50 N/m.

The modeling platforms generated by the methods disclosed herein were used to test the correlation of an applied mechanical force and tissue growth. As further detailed below and in Example 2, computational models were validated with experimental measurements using spring-mediated distraction enterogenesis in a porcine model. The study also illustrated that the modeling platforms can include patient biometrics to estimate an individual's tissue response to spring-mediated distraction enterogenesis.

In brief, results of the study presented in Example 2 suggest that not only is there a biomechanical feedback between axial mechanical force and lengthening but also a strong correlation between this mechanical force and changes in the thickness of the intestinal layers. Observations showed the muscularis layer to be substantially more affected from the mechanical force than the non-muscularis layer. In contrast, for the non-muscularis layer, a rapid increase occurred during the first 7 days after spring placement, where this behavior continued with a slower rate from post-operative day 7 to post-operative day 14. This may be due to the different behavior of muscularis and non-muscularis layers in thickening rates due to their different mechanical properties.

The study in Example 2 also investigated the biomechanics of distraction enterogenesis using computational modeling coupled with in vivo experiments. Finite element models were developed to simulate distraction enterogenesis based on continuum mechanics. The models also included tissue growth as a function of stress experienced by the tissue. The model was developed by considering the different material properties of the different layers of the intestine. The computational model was developed with experimental measurements and was additionally validated with further tests. These included studying the tension in tissue by making incisions in the intestine, and tissue strain aided by addition of color markers. The incision model was able to predict the incision opening ratio (L) reasonably well compared to corresponding experimental results. Strain measurements were also compared between model and experiments. Because the dominant force from spring expansion was in the axial direction, the model may predict higher strain value in the axial direction. The trends given by the model closely approximated the experimental results.

The study in Example 3 expands the experimental data and analysis to predict required mechanical forces to achieve double elastic lengthening for small intestines any potential size in human subjects. As is detailed in the Example, a variation was observed for small intestine geometrical characteristics such as thickness and diameter. The thickness of each layer of intestinal wall was measured where about 75% of wall was the mucosa while the submucosa and muscularis propria comprised of at or about 5% top at or about 20% of the total thickness, respectively.

The experimental results on mechanical characterization of intestinal tissue show that different layers of intestinal wall have different mechanical properties, due to the differences in their biological contents. These data also suggest differences between the mechanical properties of human intestinal tissues versus comparative animal tissues. Human intestinal tissue was observed to have significantly stiffer tissue compare to, for example, porcine tissues. The ratio between Young's modulus of different layers of intestinal wall from these mechanical characterizations were used in the computational models.

A series of computational models were developed to cover the full range of geometrical characteristics variation of human small intestine. These models were used to simulate the ranges of biomechanical response of intestinal tissue to applied force ranges. Due the differential mechanical properties of the layers, the stress and strain of these layers varied. These computational models were used to estimate the required mechanical force for distraction enterogenesis for each potential small intestinal size. The required forces varied from the smallest and thinnest to the largest and thickest intestine where this force has an approximately linear relationship with respect to the thickness and diameter of small intestine.

This is the first study of distraction enterogenesis that utilizes a computational modeling platform refined by experimental observations to predict the required force to build the medical devices, in this case the self-expanding intraluminal spring. These predicted forces can be used to calculate the spring constant based on Hooke's law for the design of the geometrical spring characteristics. Modeling becomes critically important for predicting clinical responses including elastic deformation and tissue proliferation. The model can be scaled based on patient size, intestinal diameter and thickness, and can incorporate spring characteristics for accurate predictions. This proposed use depends on the concept of scalability and assumes one can rescale the required force for intestinal tracts of different sizes. This computational modeling platform provides for reduced risk and uncertainty in surgery by defining optimal spring characteristics (e.g., spring diameter, number of turns, thickness of spring wire, etc.) based on individual patient metrics. This platform also can be used to assist surgeons to investigate the outcomes of optional surgery conditions such as, for example, the use of multiple springs in series in a subject, implantation of springs in a subject with adaptive features, and/or different loading scenarios that provide insights into clinical outcomes of the use of distraction enterogenesis as detailed herein.

As a biomedical solution for SBS, an intraluminal spring force lengthens intestinal segments. Knowing the magnitude of this mechanical force is crucial to achieve successful lengthening while minimizing tissue damage. Properties of human intestinal tissue have been mechanically characterized as bulk and as separate layers of the intestinal wall. Further, geometric metrics related to application of distraction enterogenesis in a variety of different patients having different sized intestinal tracts have been identified. These experimental measurements have been used to develop a series of computational models to cover the whole range of small intestine sizes for human subjects. These models have been used to predict the required force for the intraluminal spring customization for each patient.

The modeling methods described herein may be useful in predicting clinical responses including elastic deformation and tissue proliferation. The models can be translated based on such parameters as patient size, bowel diameter, and thickness, and can incorporate spring characteristics for more accurate predictions. This could reduce the risk and uncertainty in surgery by defining optimal spring characteristics (e.g., spring diameter, number of turns, and spring force) based on individual patient parameters, e.g., patients having intestinal tracts of different sizes.

The modeling platforms and methods may further be used as a tool to develop models in different diameters or even intestinal thicknesses to predict the tissue response in different conditions and under different mechanical forces to optimize conditions for obtaining desired tissue lengthening. Additionally, the modeling platforms and methods may be used to help surgeons investigate different surgical conditions such as multiple springs in series, implantation of springs with adaptive features, different loading scenarios (different lengths, different spring stiffness) that might give some insight into the clinical application of distraction enterogenesis.

EXAMPLES

The following examples are illustrative only, and should not be construed as limiting the disclosure in any way.

Example 1: Optimizing Spring-Mediated Lengthening by Altering the Degree of Plication The study detailed below demonstrated that a 50% reduction in intestinal diameter may be optimal in both securing springs for intestinal lengthening while also avoiding symptoms of intestinal obstruction. The study further showed that dissolvable sutures may be used to achieve intestinal lengthening, and at two months post-operatively, may allow for the natural expulsion of the springs out of the animal, which avoids a second operation for spring retrieval. These optimizations of spring-mediated lengthening offer improved strategies for developing potential therapies for SBS.

Materials and Methods. Springs were made from 0.02 gauge nickel-titanium (Nitinol) wire (McMaster-Carr, Santa Fe Springs, CA). These were placed inside size 13 gelatin capsules (Fisher Scientific, Pittsburgh, PA). The capsules were then coated with cellulose acetate phthalate (Eastman Chemicals, Fairfield, NJ). All pigs used were 4-8 week old female juvenile mini-Yucatan pigs weighing 9-13 kg (S&S Farms, Ramona, CA).

Spring Preparation. Springs were made over a 1.3 cm diameter mandrel with grooves. Nitinol wire with a 0.02 inch diameter was wrapped around the mandrel and was shape-set by heating to 500° C. for 20 minutes. It was then rapidly cooled by submerging under water. The final springs were 7.5 cm in length with 12 revolutions total, for a pitch of 0.625 cm. Spring constants were 6-8 N/m. Size 13 gelatin capsules were trimmed down and shaped to a final length of 1.5 cm. Springs were compressed and placed inside the capsules, and then the capsules were coated with cellulose acetate phthalate (CAP) to slow the dissolution of the capsule inside the intestine.

Surgical Procedure. Pigs were anesthetized with inhaled isoflurane and intubated (n=12). Their abdomens were sterilely prepped and draped, and a midline laparotomy incision was made. The jejunum was externalized, and a segment 50 cm distal to the Ligament of Treitz was identified. An anti-mesenteric enterotomy was made here, and an encapsulated spring was placed 10 cm proximal to the enterotomy. Next, the procedures varied depending on the specific experiments.

Varying Degrees of Plication. In this experiment, there were three groups total, and in all groups plication with 4-0 permanent (non-biodegradable) suture was used to confine the springs within the intestine (n=6). In the first group (n=1), 10% plication was performed to decrease the diameter of the bowel from 1.5 to 1.3 cm. In the second group (n=2), 30% plication was performed to decrease the diameter of the bowel from 1.5 to 1.0 cm. In the third group (n=3), 50% plication was performed to decrease the diameter of the bowel from 1.5 to 0.7 cm. All pigs were euthanized three weeks post-operatively, and were kept on a liquid diet of Ensure (Abbott Laboratories, Abbott Park, TL).

Dissolvable Sutures for Plication. In this experiment, there were two groups total, and in both groups plication with 4-0 dissolvable (biodegradable) suture was used to secure the springs within the intestine (n=6). In the first group (n=3), 50% plication was performed to decrease the diameter of the bowel from 1.5 cm to 0.7 cm, and pigs were euthanized three weeks post-operatively. They were kept on a liquid diet of Ensure. In the second group (n=3), 50% plication was performed to decrease the diameter of the bowel from 1.5 cm to 0.7 cm, and pigs were euthanized two months post-operatively. They were kept on a liquid diet for three weeks, and then advanced to a regular diet for the remainder of the time.

In all the above experiments, there were two plication sutures placed on the proximal side of the spring, and four plication sutures placed on the distal side of the spring to reduce the chance of distal passage of the spring. The inner most plication sutures around the spring measured 1.5 cm apart. These were marked by injecting India ink, so that lengthening could be assessed at the time of euthanasia. Metal clips were placed in the mesentery of the spring segments so the site of spring implantation could be monitored radiographically. The enterotomy was then closed with a series of interrupted sutures, the intestine returned inside the abdomen, and the abdomen was closed in layers.

Radiographic Evaluation. Abdominal plain film radiographs were taken every week to evaluate for spring re-expansion and spring positioning. The metal clips placed in the mesentery at the time of the original operation were used to identify the starting location of the springs.

Gross and Histological Evaluation. Once the pigs were euthanized, segments of jejunum containing the springs were evaluated for lengthening and also prepared for histologic examination. Adjacent segments of normal jejunum not containing springs were also evaluated for comparison. Histologic preparation was done by leaving the jejunal segments in 10% buffered formalin (Fisher Scientific, Pittsburgh, PA) for at least 24 hours. The samples were then cut into cross-sections and these were imbedded in paraffin. The paraffin blocks were cut into 5 μm sections and placed onto slides to be stained with hematoxylin and eosin. The slides were examined under 4× magnification using brightfield microscopy. Representative photographs were taken. Crypt depth and muscularis propria thickness were measured at four points per sample.

Statistical Analysis and Results. All data were reported as means and standard deviations. Two-tailed paired and unpaired Student's t-tests were used to analyze lengthening and histologic results, respectively.

All pigs tolerated their operations without complications. Post-operatively, they experienced a recovery period of several days where they had decreased appetites, but were subsequently able to tolerate liquid diets without any signs of obstruction. There were no cases of perforation. At three weeks, pigs were introduced to solid food and slowly advanced to regular diets, which they also tolerated without complications. Average weight gain over three weeks was 2.5±1.7 kg, and average weight gain over two months was 14.3±2.1 kg.

Following surgical implantation with varying degrees of plication, springs were followed radiographically to monitor for expansion and movement. 10% and 30% plications resulted in quicker spring re-expansion than a 50% plication based on radiographic measurements. One week post-operatively, springs secured with 10% and 30% plications had average lengths of 5.7 cm and 6.0 cm, respectively. Springs secured with a 50% plication had average lengths of 4.8 cm. Two weeks post-operatively, springs secured with 10%, 30%, and 50% plications had average lengths of 6.8, 6.3, and 6.0 cm, respectively, based on plain film radiographs.

Pigs were euthanized, and segments of jejunum containing springs were evaluated for lengthening. A 10% plication resulted in a 1.3-fold increase in length, a 30% plication resulted in a 1.8-fold increase in length, and a 50% plication resulted in a 2.7-fold increase in length ($p<0.05$). This corresponds to an absolute gain of 0.5, 1.25, and 2.9 cm per spring for 10%, 30%, and 50% plication respectively.

Histologic analysis showed that all springs caused significant increases in both crypt depth and muscularis propria thickness compared to normal unlengthened segments of jejunum, regardless of the degree of plication. Normal jejunum had an average crypt depth of 266±58 μm, while lengthened segments had an average crypt depth of 553±62 μm with 10% plication, 396±88 μm with 30% plication, and 492±80 μm with 50% plication ($p<0.001$ for each plication segment relative to control). Normal jejunum had an average muscularis propria thickness of 227±75 μm, while lengthened segments had an average muscularis propria thickness of 433±61 μm with 10% plication, 510±129 μm with 30% plication, and 484±65 μm with 50% plication ($p<0.001$ for each one relative to control).

Following spring implantation with dissolvable sutures, spring lengths were again monitored with plain films. There was gradual expansion of the springs, with average lengths of 5.1 cm at one week post-operatively, and 6.4 cm at two weeks post-operatively. Half of the pigs (n=3) were then followed for two months; at one month post-operatively the springs appeared to be maximally expanded at 7.3 cm. Two of the three pigs passed the springs out of their intestines between post-operative day 50 to 60. One pig retained the spring in place throughout the entire two month period.

Pigs were euthanized and segments of jejunum were examined for lengthening at three weeks and at two months post-operatively. At three weeks, there was an average 2-fold increase in length, and at two months there was an average 1.7-fold increase in length ($p<0.05$, length at 2 months compared to length at start). This represented an average gain per spring of 1.5 cm and 1.1 cm, respectively.

Review of histology showed significant changes of all spring-containing segments at both three weeks and at two months post-operatively, compared to normal jejunum that was not lengthened. Normal jejunum had an average crypt depth of 202±39 μm and 216±44 μm at three weeks and two months, respectively. Lengthened segments had an average crypt depth of 444±75 μm and 449±69 μm at three weeks and two months, respectively ($p<0.001$ for each one, relative to normal). Normal jejunum had an average muscularis propria thickness of 227±46 μm and 216±40 μm at three weeks and two months, respectively. Lengthened segments had an average muscularis propria thickness of 550±109 μm and 396±101 μm at three weeks and two months, respectively ($p<0.001$ for each one, relative to normal).

Example 2: Modeling to Develop Platform for Predicting the Force Required for Lengthening This study investigated the biomechanics of distraction enterogenesis using computational modeling coupled with in vivo experiments. The models included tissue growth as a function of stress experienced by the tissue. The model was also developed by considering the different material properties of the different layers of the intestine. The computational model was developed with experimental measurements and was additionally validated with further tests. These included studying the tension in tissue by making incisions in the intestine, and tissue strain aided by addition of color markers. The incision model was able to predict the incision opening ratio (L) reasonably well compared to corresponding experimental results. Strain measurements were also compared between model and experiments.

The modeling methods described here may be useful in predicting clinical responses including elastic deformation and tissue proliferation. The models may also be translated based on such parameters as patient size, bowel diameter, and thickness, and may incorporate spring characteristics for more accurate predictions.

Materials and Methods. Placement of in-continuity small bowel springs for distraction enterogenesis was performed on 4-6 week old female Yucatan pigs weighing 7-10.5 kg. In brief, juvenile pigs ages four to six weeks were placed under general endotracheal anesthesia and underwent midline laparotomy. An enterotomy was performed to facilitate placement of an encapsulated, compressed nitinol spring in the proximal jejunum. Biocompatible nickel-titanium (Nitinol) springs were created as has been described in Example 1. Briefly, 0.02 inch gauge nitinol wire (McMaster-Carr, Santa Fe Springs, CA) was wrapped around a 1.3 cm diameter mold, heated to 500° C. for 30 minutes, rapidly cooled under water. Springs were cut to 7.5 cm in length and included an average number of 12 coils. The compressed springs were then placed in an absorbable gelatin capsule (Fisher Scientific, Pittsburgh, PA) with a diameter of 1.3 cm and a length of approximately 1 cm and coated with cellulose acetate phthalate (Eastman Chemicals, Fairfield, NJ) to delay capsule degradation and subsequent spring expansion. Nitinol springs were chosen given the customizability and ease of generating the spring. Furthermore, Nitinol is a biocompatible metal that is already used in medical devices, which facilitates the use of Nitinol springs for future clinical applications. Spring characteristics including uncompressed length, spring constant and diameter were measured preoperatively. The spring was confined within the bowel by plication sutures (4-0 prolene) that were placed to narrow the lumen of the bowel by approximately 50%; two sutures were placed proximally and four distally. After spring placement, animals were maintained initially on a liquid diet and were advanced to full feeds after two weeks.

Histology. Pigs were euthanized on day 7 and 14 after the original operation. Normal segments and segments of intestine containing the springs were removed and evaluated for lengthening as well as for histologic examination. Intestinal segments were placed in 10% buffered formalin (Fisher Scientific, Pittsburgh, PA) overnight. Samples were then cut into cross-sections and imbedded in paraffin. Paraffin blocks were cut into 5-μm sections to create slides that were stained with hematoxylin and eosin (H&E). The thickness of each layer of intestinal wall was measured at multiple representative locations on each slide and averaged to calculate the mean for each section.

Measurements of Tissue Strains: in Vivo Immediate Spring Release. In order to measure the immediate elastic response that occurs after spring deployment, additional Nitinol springs were placed in a distal segment of bowel just prior to scarification. As before, animals were placed under general anesthesia and a distal segment of bowel (away from the initial spring segment) was eviscerated. An enterotomy was performed and a compressed Nitinol spring without a capsule was placed within a plication segment of bowel. Prior to release of the spring, a marking pen was used to mark points on the bowel wall to aid in tracking the immediate expansion. Video was recorded continuously from the time of spring deployment and coordinates of the marked dots were traced over time to be used as inputs for customized MATLAB code to analyze the elastic strains of the bowel.

Incisional Experiment. One of the challenges of distraction enterogenesis is implementing the method for different intestinal sizes. The translatability of the distraction enterogenesis method was previously tested successfully by performing the experiments on animals with different intestinal sizes such as mouse, rat, and pig. To investigate translatability of the computational modeling described herein, a computational mouse model was first developed and then tested with incision experiments as follows.

To characterize stress in the intestinal tract, experiments were performed in four C57BL/6 mice weighing 16-29 g (Jackson Laboratory, Bar Harbor, ME). Mice were anesthetized with inhaled isoflurane and a midline laparotomy was performed. The small bowel was exteriorized, and bowel clamps were placed 1-2 cm apart in order to maintain tension at the injection site. Using an insulin syringe, 10-15 mL of warmed, liquid HistoGel was injected into the clamped bowel segment and allowed to rest until semi-solidified. A series longitudinal and transverse incisions were made using a 15-blade scalpel on the anti-mesenteric surface of the bowel. The procedure was repeated in adjacent bowel sections. Photos and video were obtained of the bowel before and after injection and incision to measure the initial length of the incision and opening ratio. Incision length (L) and opening width (W) were used to compute opening behavior for each wound. The incision opening ratio (L) was calculated for comparison with modeling results.

Statistical Analysis and Computational Methods. Experimental results were analyzed with descriptive statistics. Data were expressed as mean values±standard deviations. Two-way ANOVA tests were used for statistical analysis of lengthening data and histologic data. Finite element analysis has been extensively used to study problems with a wide range of biomedical applications in different organs of body. In this study, computational models for distracted enterogenesis and enterotomy experiments were developed using the commercial finite-element software ABAQUS (version 2017, SIMULIA, Providence, RI) using implicit solver. Constitutive relations (material properties) and tissue proliferation were defined via the ABAQUS user subroutine UMAT.

Overview of Computational Models. Model geometry was based on measurements from histology slides of pig and mouse intestine. Pig intestinal tract was considered as a cylindrical hollow with dinner=7 mm and douter=8 mm, while the initial length of distracted segment was chosen similar to the distracted segment in experimental set up. For mouse models, intestinal tract was considered as a cylindrical hollow with dinner=1.75 mm and douter=2 mm. In both pig and mouse models, wall thickness was divided into two layers: muscularis and non-muscularis (mucosa, muscularis mucosa and submucosa). The non-muscularis layer was designated to be three times thicker than muscularis layer. This division was chosen based on the experimental observations for the histology images.

Distraction Enterogenesis Model. Appropriate boundary conditions were enforced for the right end of distracted segment and the bottom part for the mesentery layer throughout the simulation. The right end of the spring and distracted segment was fixed while the other ends are free for spring compression and tissue stretch steps. Since the base of the mesentery has very limited movement in vivo, this end of the mesentery layer was fixed throughout the simulation.

The model included three steps: a) spring compression, b) plication (diameter reduction of intestinal tract) and c) spring expansion. During the first step, spring was compressed while a surface to surface frictionless contact, with normal and tangential behavior interface chosen as Hard Contact and Frictionless Contact respectively, was defined between plication and distracted segments. Once the spring was fully compressed, the plicated and distracted segments were adhered together. In the second step, the diameter of tract was reduced by 50% using applied force on the anti-mesenteric side of the plicated segment. During the final step, the spring was released and allowed to expand, while the plicated and distracted segments remain adhered together. As the spring lengthened, it stretched the distracted tissue therefore generating elastic tissue deformation. In addition to this elastic deformation, the mechanical distraction triggered the tissue proliferation component that was implemented within the model as a secondary source of lengthening. Tissue growth details are further explained below.

Tetrahedral elements (C3D4) were used for all parts of distraction enterogenesis model. The full model was approximately discretized into 165,000 elements with 62,000 nodes.

Incisional Model. Here the model was fixed between two clamps. For each incision model, first internal pressure was applied to the internal surface to result in a similar inflation ratio (RO) to its corresponding incision experiment where R and RO are the radii before and after inflation. In each incision model, once the corresponding inflation ratio was achieved then each incision length was chosen to be similar to its experiment measurements. While the incision length and inflation ratio (internal pressure) are the same between model and experiment, the incision opening ratio (L) predicted by the model was compared to its corresponding experimental ratio.

For the incision models, hexagonal elements (C3D8) were used where the model was approximately discretized into 35,000 elements with 90,000 nodes. Testing with finer meshes confirmed that the chosen mesh size was accurate enough for the present purposes.

Results. As previously mentioned, the study in this example focuses on studying biomechanics of distraction enterogenesis using a self-expanding spring. Pigs and mice were used as the animal models to lengthen the small intestine using mechanical force of the spring. Next, computational modeling was employed to determine the physical plausibility of lengthening. Finally, additional experimental data was used to test the model.

Histological Changes of the Intestine During Distraction Enterogenesis. Intestinal lengthening and thickening was observed after short (7 days) and longer (14 days) time periods after spring placement. The lengthening ratio for day 7 (n=4) and day 14 (n=3) was 2.14±0.71 and 2.9±0.1, respectively. Normal jejunum showed an average thickness of 263±40 μm and 667±97 μm for muscularis and non-muscularis layers, respectively, whereas distracted segment of jejunum showed an increase in thickness of both muscularis and non-muscularis layers on different post-operative days. The average thickness of muscularis for the distracted segment of jejunum was 457±81 μm and 756±232 μm for post-operative days 7 and 14, respectively. The observed thickness of non-muscularis layer for distracted segment of jejunum was 1000±300 μm and 1200±116 μm for post-operative days 7 and 14, respectively.

Computational Model for Distraction Enterogenesis. Similar to the experimental process, the simulation of distraction enterogenesis began by compressing the spring, where the external force was applied to the left end of spring in the axial direction. Self-contact was defined for the spring surfaces to prevent the self-penetration of different coils of spring. After a similar process for spring compression, from fully relaxed to fully compressed, compare to experiment, the plicated segment contacted the distraction segment and due to defined surface to surface contact between these parts, they adhered together for the remainder of the simulation. After the compression, the diameter of the intestine was reduced by 50% on the anti-mesenteric side of the plication segment. Finally, the spring was released to enable the intestinal expansion. As the spring expanded, it stretched the distraction tissue to increase its length. Tissue response to the applied force had elastic and proliferative components. To model proliferation, tissue growth in both radial and axial directions was modeled as a function of the axial stress experienced by the distracted segment. Similar to the experimental observations, different growth rates were employed for the non-muscularis and muscularis layers, with the muscularis layer growing more than the non-muscularis layer. From the results, it appears that both elastic and growth components of the tissue response were a factor in lengthening, however, it is important to point out that the elastic component corresponded to an instant tissue response while the growth component corresponded to tissue response to the mechanical stimulation over a longer time period.

Tissue Strain. Markings placed on the jejunum allowed tracking of spring expansion immediately after deployment but did not allow for tracking tissue deformation over extended periods of time. Because tissue response to the mechanical force occurs over a longer time frame (weeks not minutes), this immediate response of tissue to mechanical force only represents elastic deformation. For the remainder of the strain experiments, coordinates of the markers were used to calculate 2D strains with an average $E_{xx}=0.2\pm0.08$ and $E_{yy}=0.1\pm0.09$ for $L/L_0 \approx 1.21$ and $E_{xx}=0.43\pm0.13$ and $E_{yy}=0.09\pm0.08$ for $L/L_0 \approx 1.35$. Horizontal and vertical direction were chosen for X and Y direction respectively.

The computational models were validated with other experimental measurements. Here the results of experimental mechanical perturbations were used to test the ability of the distraction enterogenesis model to match experimental strain measurements. To compare the experimental strain values with model prediction, a full distraction enterogenesis model was used. For this purpose, growth was turned off and the model was stopped when lengthening ratios were similar to experiments, and then model strains were compared with experimental measurements. Results of the model prediction were in a good agreement with experimental strain values for different different lengthening ratios.

Example 3: Biomechanical Force Prediction for Lengthening of Small Intestine During Distraction Enterogenesis The experimental results on mechanical characterization of intestinal tissue suggest that not only do mechanical properties of human intestinal tissues differ from those of animals but also that different layers of intestinal wall have different mechanical properties due to the differences in their biological contents. Human intestinal tissue was observed to have significantly stiffer tissue compare to porcine tissues, and the ratio between Young's modulus of different layers of intestinal wall from these mechanical characterization were used in the computational models.

Figures 4A, 4B, 4C:
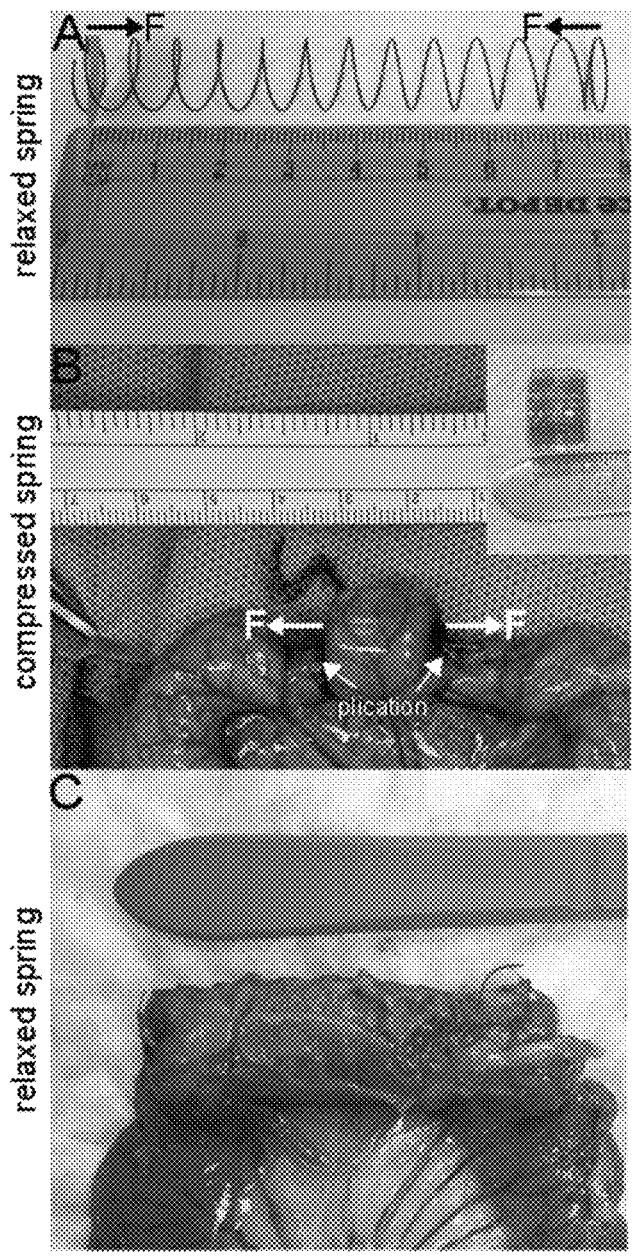
FIGS. 4A-4C provide representative images for distraction enterogenesis experimental set up using an intraluminal spring: (4A) Relaxed spring; (4B) Intra-operative image demonstrating compressed encapsulated spring within a segment of small intestine held in place with two plication sutures; and (4C) Distracted segment of small intestine with expanded intraluminal spring at time of tissue retrieval.

Spring Production and Encapsulation. Biocompatible nickel-titanium (nitinol) springs were created where 0.02 inch gauge nitinol wire (McMaster-Carr, Santa Fe Springs, CA) was wrapped around a 1.3 cm diameter mold, heated to 500° C. for 30 minutes, rapidly cooled under water. Springs were cut to 7.5 cm in length, and spring constants measured (FIG. 4A). Springs were compressed and placed within an absorbable gelatin capsule (Fisher Scientific, Pittsburgh, PA) then coated with cellulose acetate phthalate (Eastman Chemicals, Fairfield, NJ), which allows for delayed gelatin capsule degradation (FIG. 4B).

Animal and Human Sample Preparation and Surgical Procedure. Animal surgeries and care were approved by Stanford Administrative Panel on Laboratory Animal Care (protocol 32278). Four- to six-week old juvenile female Yucatan pigs (S&S Farms, Ramona, CA) underwent intervention. Animal subjects underwent general anesthesia and were sterilely prepped and draped. A midline laparotomy incision was made, the jejunum identified 50 cm from the Ligament of Treitz. An anti-mesenteric longitudinal incision was made at this point in order to introduce an encapsulated spring. India ink was injected into the submucosa to identify a 1.5 cm long segment to identify the region of compressed spring-loaded capsule (FIG. 4B). Once the capsule was introduced to this marked segment, the bowel was plicated to 50% of bowel diameter to ensure the expanded spring remained in place: proximally by two 4-0 polypropylene interrupted sutures and distally by four sutures. The enterotomy was then closed primarily, the small intestine returned into the abdomen, the abdomen irrigated, and the incision closed in multiple layers. Animals were provided with liquid diets for the first post-operative week.

Figure 5:
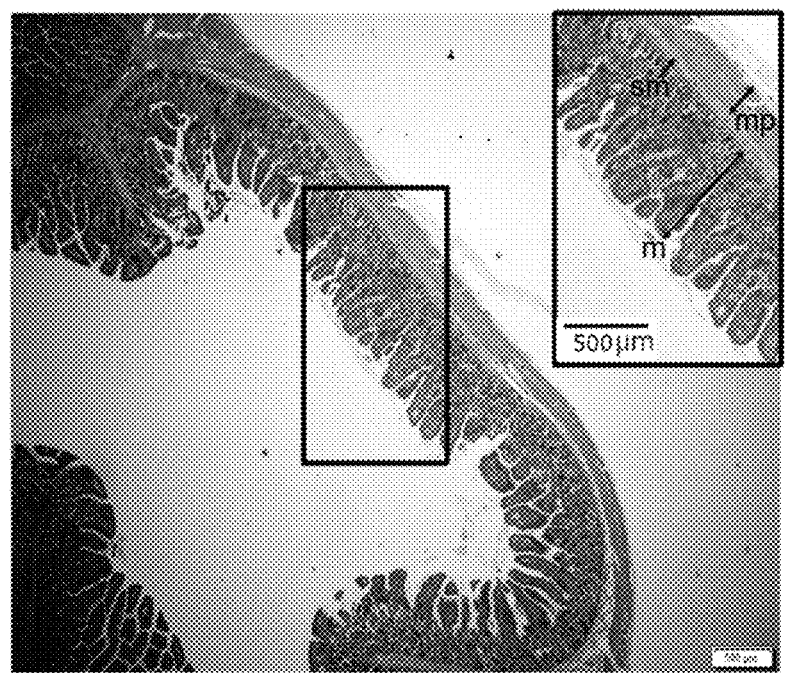
FIG. 5 provides representative cross-sectional light micrographs of H&E stained jejunum under normal (zero force) conditions. Black arrows indicate major layers intestinal wall as mucosa (m), submucosa (sm) and muscularis propria (mp).

Geometrical and Histologic Evaluation. Pigs were euthanized, and bowel segments were retrieved. Normal segments and segments of intestine containing the springs were removed and evaluated for lengthening as well as for histologic examination. Intestinal segments were placed in 10% buffered formalin (Fisher Scientific, Pittsburgh, PA) overnight. Samples were then cut into cross-sections and imbedded in paraffin. Paraffin blocks were cut into 5-µm sections to create slides that were stained with hematoxylin and eosin (H&E) (FIG. 5). The thickness of each layer of intestinal wall was measured at multiple representative locations on each slide and averaged to calculate the mean for each section.

For human samples after the collecting the samples, they were rinsed with saline to remove intestinal content and then were placed in phosphate buffered saline (PBS) on ice kept to keep them fresh. First they were flattened on a glass slide to perform diameter and thickness measurements using fine caliper then each sample was prepared either for mechanical characterization or H&E staining. Specimens for mechanical testing continued to be kept in PBS while samples for H&E staining underwent similar process as pig specimens as described above.

Mechanical Characterization. Immediately after euthanizing the animal, a laparotomy was performed to remove 10-20 cm segment of jejunum. Specimen was rinsed with saline to remove intestinal content and the specimen was placed in PBS on ice. Segments of freshly harvested porcine small intestine were stored in PBS prior to uniaxial tensile testing. Cylindrical intestinal tract was cut open (FIG. 7A), and longitudinal cuts were made to obtain the elastic modulus of the small intestine in the longitudinal direction. To perform mechanical testing for intact tissue no further procedure was needed. For mechanical characterization of submucosa and muscularis layers together, the mucosal layer was removed using a glass slide to scrape off the mucosa. In another set of mechanical testing for the submucosal layer, both mucosal and muscularis layers were removed from both sides of submucosa.

Tensile tests were performed using an Instron type 5565, with a 1 kN load cell to measure the elastic modulus. Specimens were clamped using special custom-made anti-slip grips to counteract any slipping (FIG. 7B). A pre-load of 2 N was then applied at a displacement of 0 mm to eliminate slack within the sample. After pre-load step, the force and displacement measurements were stored using the controlling software while the mechanical load was stretching the specimen due to applying axial mechanical force. The test was stopped once failure was observed in the force-displacement plot (FIG. 7C).

Computational Methods and Models. Model geometry was based on measurements from histology slides and geometrical measurements of intestinal tissue (FIGS. 5, 6). The intestinal tract was considered as a cylindrical hollow area, while a thinner layer was tied to the main cylindrical part as the mesentery layer (FIG. 8). A series of models were developed to cover an expanded range for different radii and thicknesses based on the experimental measurements of geometrical characteristics of human small intestine (FIG. 6). The considered radius range was $R_{inner}$=0.25-3 cm while thickness of intestinal wall was varied t=0.5-3 mm while the initial length of distracted segment was chosen similar to distracted segment in experimental set up. For each computational model, the intestinal wall was divided into three main layers: mucosa, submucosa and muscularis propria (FIG. 8). Thickness of each layer compared with the total wall thickness can be represented by:

$$\frac{t_{mucosa}}{t_{total}} = 0.75, \frac{t_{submucosa}}{t_{total}} = 0.05, \frac{t_{muscularis\ propria}}{t_{total}} = 0.2.$$

The division and ratios were approximated from experimental histology images (FIG. 5).

Figure 7:
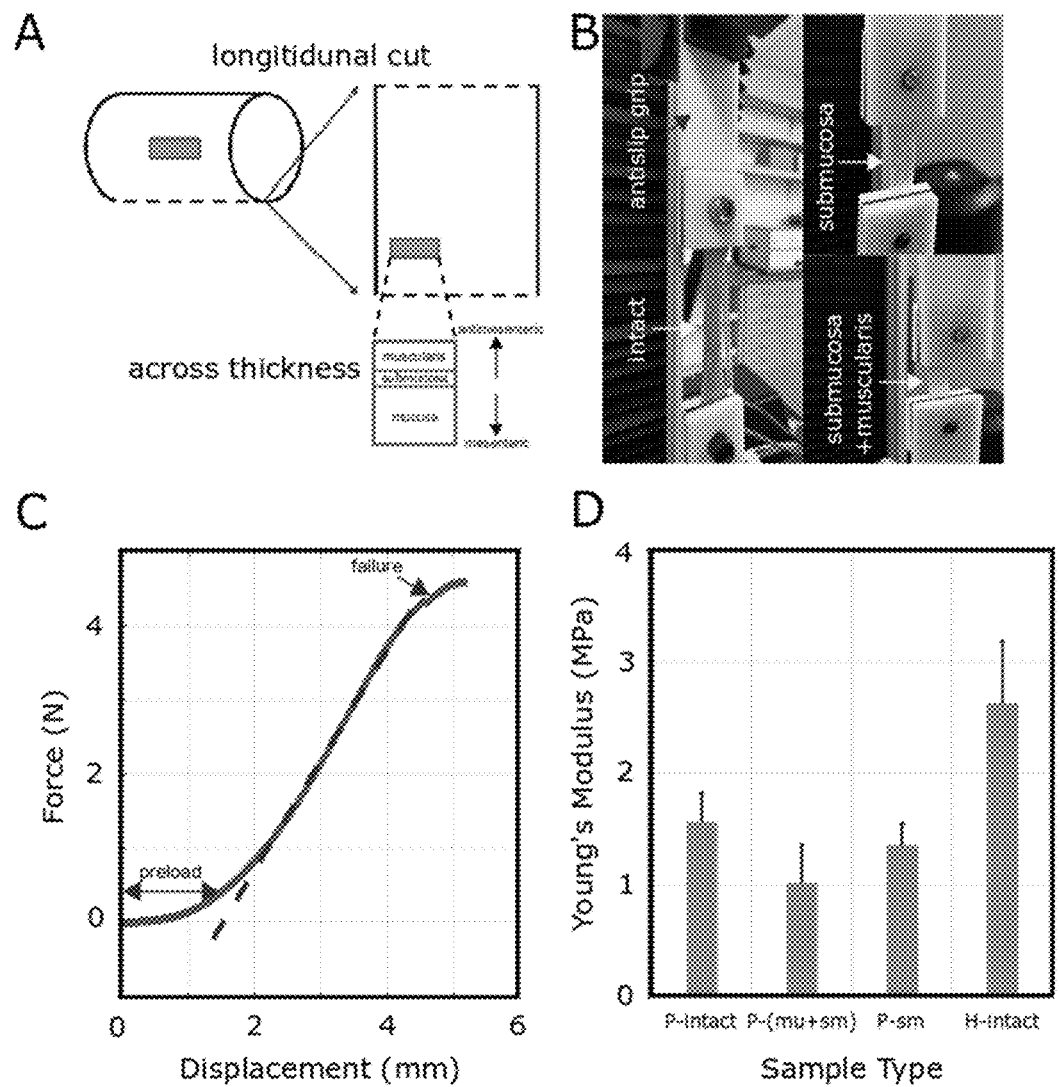
FIG. 7 provides a mechanical characterization of pig and human small intestinal tissue. (A) Schematic diagram represents how rectangle specimens were prepared from cylindrical small intestinal tract. (B) Tensile test performed using an Instron type 5565 with anti-slip grips. (C) Representative force-displacement plot of a specimens. (D) Average Young's module for pig and human.
Figure 8A:
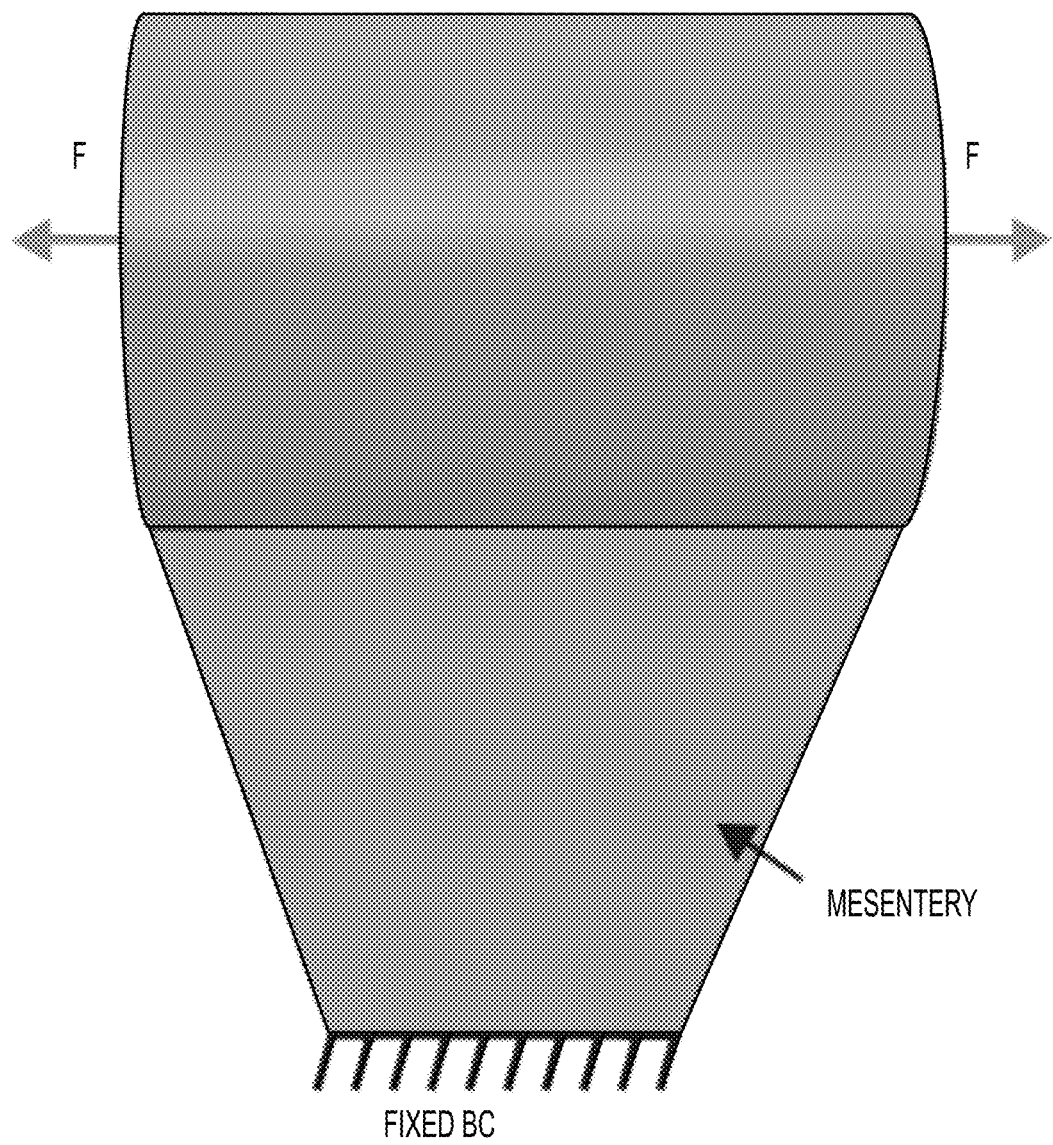
FIGS. 8A-8C provide a finite element model for distraction enterogenesis. (8A) Frontal and (8B, 8C) cross-section view of the model with mucosa, submucosa, and muscularis layers shown in red, yellow/green and red respectively in the distracted segment. Model also includes mesentery layer attached to the distracted segment on the mesentery side. Fixed boundary conditions are used for bottom end of mesentery layer. "BC" and "F" in (8A) are abbreviations for boundary condition and force.
Figure 8B:
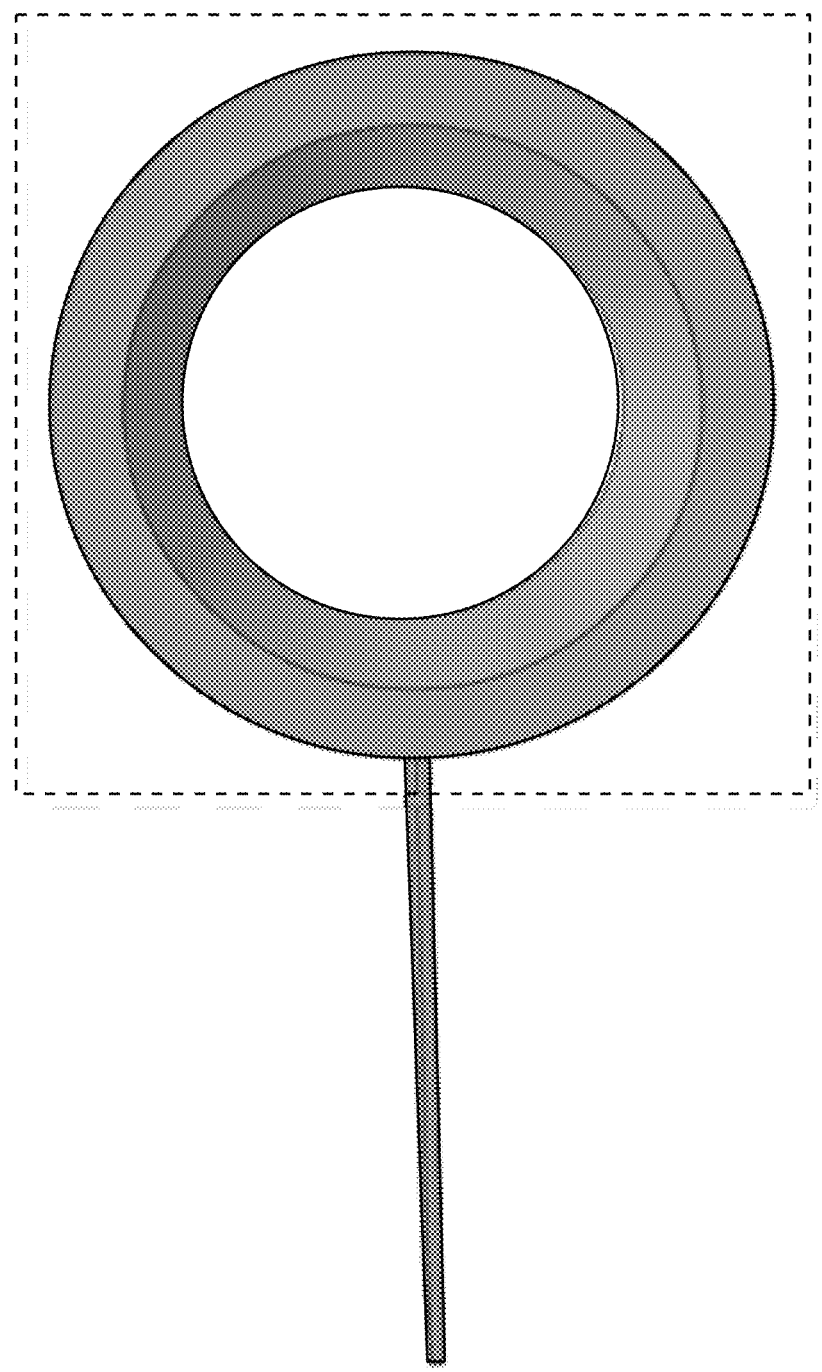
Figure 8C:
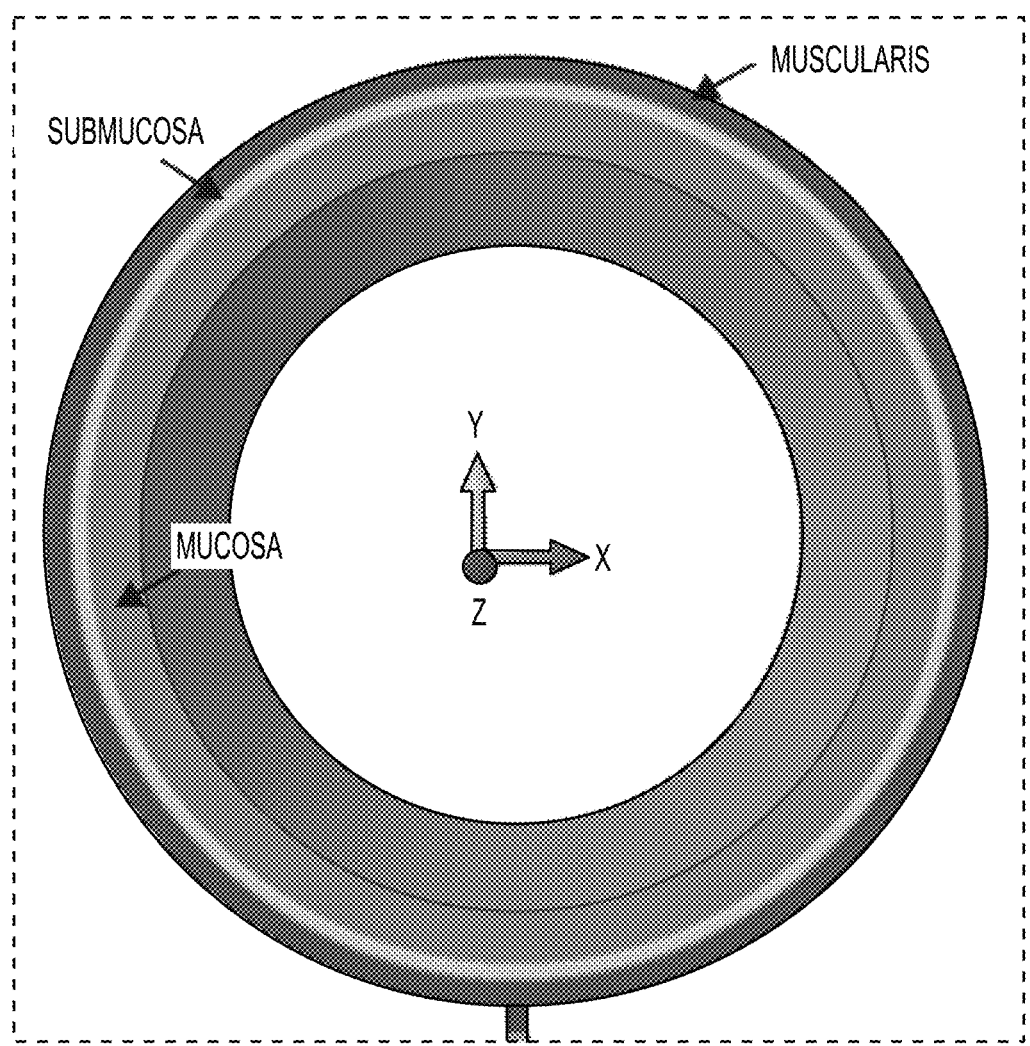

Appropriate boundary conditions were enforced for the internal surface of the hollow cylinder of distracted segment and the bottom part for the mesentery layer throughout the simulation (FIG. 8A). In the computational models, the internal surface of the cylinder was chosen to have only displacement freedom (movement in X, Y and Z directions) with no freedom to rotate, which choice was supported by experimental observation. During the secondary animal surgery to remove the springs and evaluate lengthening of distracted segment we observed that the distracted segment is still relatively straight with no sign of tissue rotation (FIG. 7). While not intending to be bound by theory, this is suspected to be due to the close physical contact of spring with internal surface of intestinal lumen. Since the base of the mesentery has very limited movement in vivo, this end of the mesentery layer was fixed throughout the simulation (FIG. 8A).

Each model starts with applying mechanical force at both ends similar to what occurs in experimental set up. This mechanical force is due to when the compressed spring starts to be relaxed and generates the mechanical stimulus where it distracts and thus stretches the tissue to lengthen it over time. As the spring lengthens, it stretches the distracted tissue and thereby generates elastic tissue deformation. In addition to this elastic deformation, the mechanical distraction triggers a tissue proliferation component. A focus of this study was to predict the required mechanical force that generates double elastic lengthening for each model with different radius or intestinal wall thickness.

In synthetic/simulated models based on observed data, hexagonal elements were used for all parts of distraction enterogenesis model for all models. For each model, testing with finer meshes confirmed that the chosen mesh size was sufficiently accurate for the present purposes.

Distraction enterogenesis processes were simulated using a continuum mechanics theory for large deformation. In brief, the theory approximates the soft intestinal tissues as pseudo elastic with negligible viscous effects. Total deformation gradient tensor F, which maps material points from the initial configuration to the deformed configuration at a later time, is decomposed as:

$$F=F^*\cdot G \tag{1}$$

where G and F* are the growth tensor (in this study G=1) and elastic deformation gradient tensor, respectively. As the tissue deforms, F maps the particles between deformed and unreformed configurations.

Because of the cylindrical shape of intestinal tract, in the initial configuration, separate cylindrical coordinate systems (R, θ, Z) are considered for distracted and plication segments. Relative to these coordinates, the growth tensor is taken in the orthotropic form:

$$F=F_R e_R e_R + F_\theta e_\theta e_\theta + F_Z e_Z e_Z \tag{2}$$

Where the $e_I$ are unit base vectors. With the tissues assumed to be slightly compressible, based on the continuum mechanics theory, the constitutive relation has the form:

$$\sigma = \frac{1}{J} F \cdot \frac{\partial W}{\partial E} \cdot F^T \quad (3)$$

Where σ represents the Cauchy stress tensor from the strain-energy density function W(E). In equation (3), J=detF is the elastic volume ratio and $$E = \frac{(F^T \cdot F - I)}{2}$$

is the Lagrangian elastic strain tensor, I is an identity tensor and T indicates the transpose. A Neo-Hookean strain-energy density function is chosen in the form:

$$W = C * (\bar{I}_1 - 3) + \frac{1}{D}\left[\frac{1}{2}(J^2 - 1) - \ln J\right] \quad (4)$$

Where C is directly related to shear modulus of the intestinal tract tissue and D represents the volumetric compliance, and $\bar{I}_1 = J^{-2/3} tr(I+2E)$ is a modified strain invariant. Model constants in equation (4) were calculated using obtained Young's modulus and Poisson's ratio as follow:

$$C = \frac{G}{2} = \frac{E}{4*(1+\vartheta)} \quad (5)$$

$$D = \frac{2}{K} = \frac{6*(1-2\vartheta)}{E} \quad (6)$$

G, K, E and ϑ are shear modulus, bulk modulus, Young's modulus and Poisson's ratio, respectively. Young's modulus (E) was obtained from mechanical characterization results while ϑ was obtained from the assumption that soft tissue behaves nearly incompressible, then using E and ϑ constants C and D were calculated for each layer of intestinal wall.

Figure 6A:
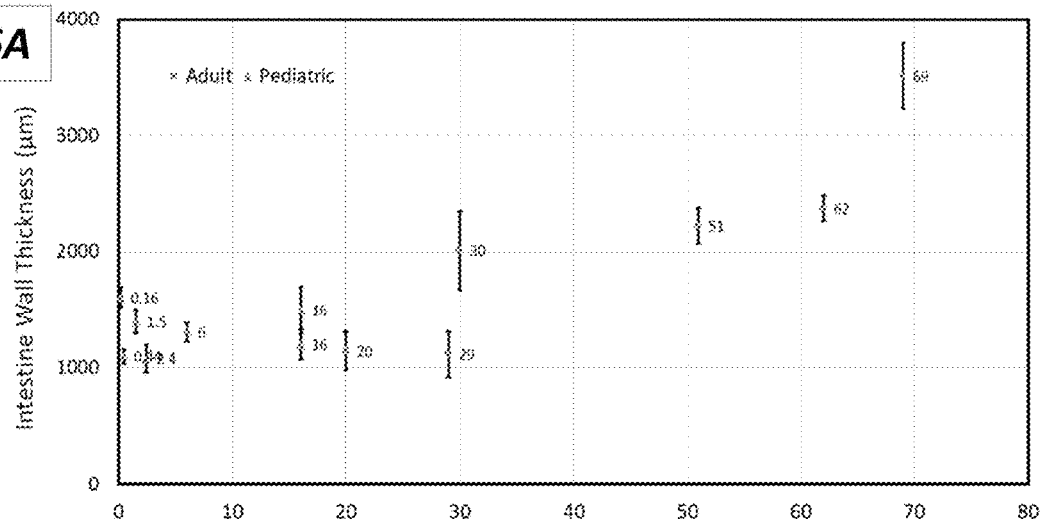
FIGS. 6A-6B provide a geometrical metrics measurements of the small intestine from a wide range of human subjects.

Geometrical Characteristics of Human Small Intestinal Tract. Small intestinal samples were collected from discarded human tissues between the age of 2 months to 69 years. Intestinal wall thickness between these subjects varied between ≈1-4 mm (FIG. 6A). Content of the intestine was washed out, and the cylindrical tract was flattened on a glass slide to measure the distance between the mesentery and anti-mesentery sides (d), which is half of the circumference of the intestine, or $$d = \frac{\text{Circumference of circular crioss section}}{2} = \frac{2\pi R}{2} = \pi R \text{ thus } R = \frac{d}{\pi}.$$

Figure 6B:
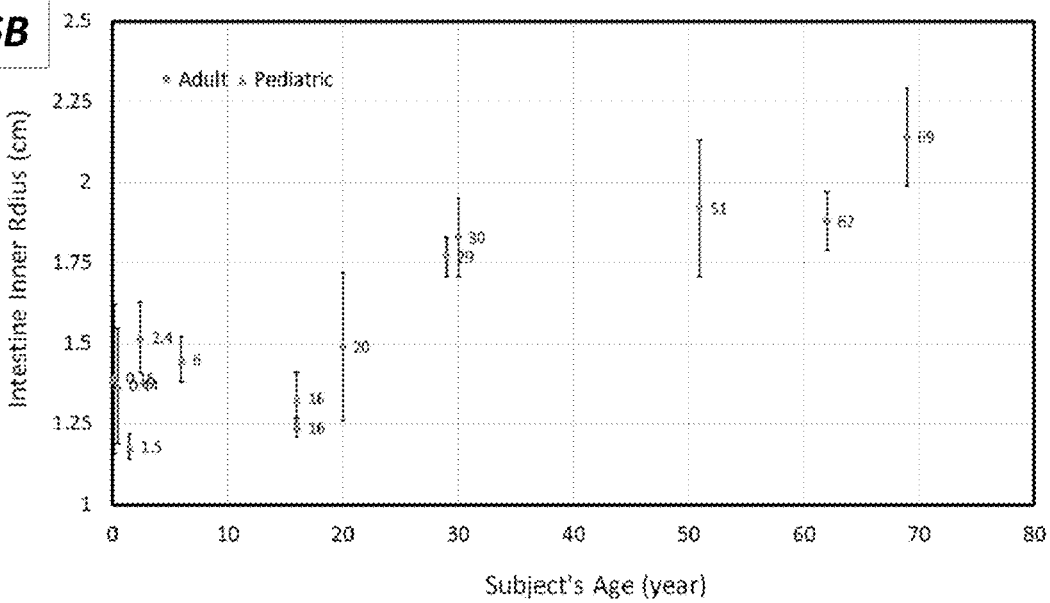

This process was repeated for all of the intestinal samples, and the range of the radii was found to be ≈1-2 cm (FIG. 6B).

Wall thickness generally increased with age, consistent with the growth of small intestine as individuals develop. Similar pattern was observed for the radius of intestine.

Mechanical Characterization of Small Intestinal Tissue. Collected data from mechanical testing on intestinal tissue of pig and human using an Instron type 5565, with a 1 kN load cell was used to calculate the mechanical properties of the tissue. First the preload and failure parts of the force-displacement plot (FIG. 7C) were removed to determine Young's modulus using the slope of fitted lines. The same post-processing calculations were repeated to determine the Young's modulus of intact or separated layers of intestinal tissues.

The averaged Young's modulus of intact intestine on pig samples was 1.56 MPa which was higher than that of both submucosa and "submucosa+muscularis propria" layers where "submucosa+muscularis propria" layers had an average of 1.01 MPa and the average Young's modulus for the submucosal layer was 1.35 MPa (FIG. 7D). The submucosal layer contains the majority of the extracellular matrix, whereas the muscularis propria layer is formed of smooth muscle fibers.

Human intestinal tissue showed significantly higher Young's modulus with an average of 2.63 MPa as compared to porcine tissue. All of the mechanically tested human tissues were from pediatric subjects. Also due to the limited source of human intestinal samples, mechanical testing was performed only on intact tissue while for pig samples mechanical characterization was completed for both intact and separated layers (FIG. 7D). The ratio of Young's modules between different layers of porcine tissue was employed for simulation purposes.

3D Computational Model for Distraction Enterogenesis. Based on observed data, a series of 3D computational models with different thickness for intestinal wall and radius were created to predict the required mechanical perturbation to achieve double lengthening of the small intestine during distraction enterogenesis. For each model, forces were applied at both ends, and the calculations were stopped when the desired double lengthening was achieved.

Figure 9A:
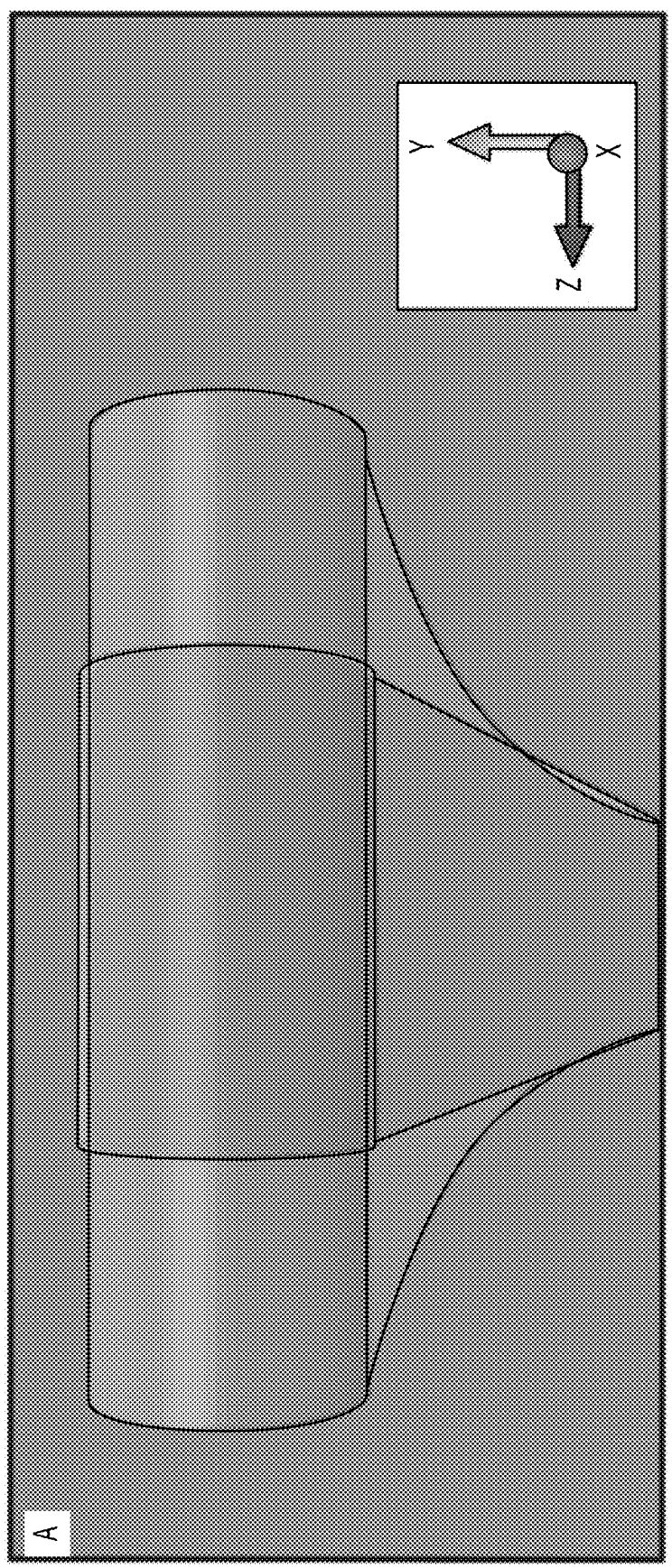
FIGS. 9A-9C provide computational model results after lengthening of distracted segment due to applied mechanical forces at both ends. (9A) Representative frontal view of model. (9B, 9C) Stress representation of computational model in R, θ, Z directions.
Figure 9B:
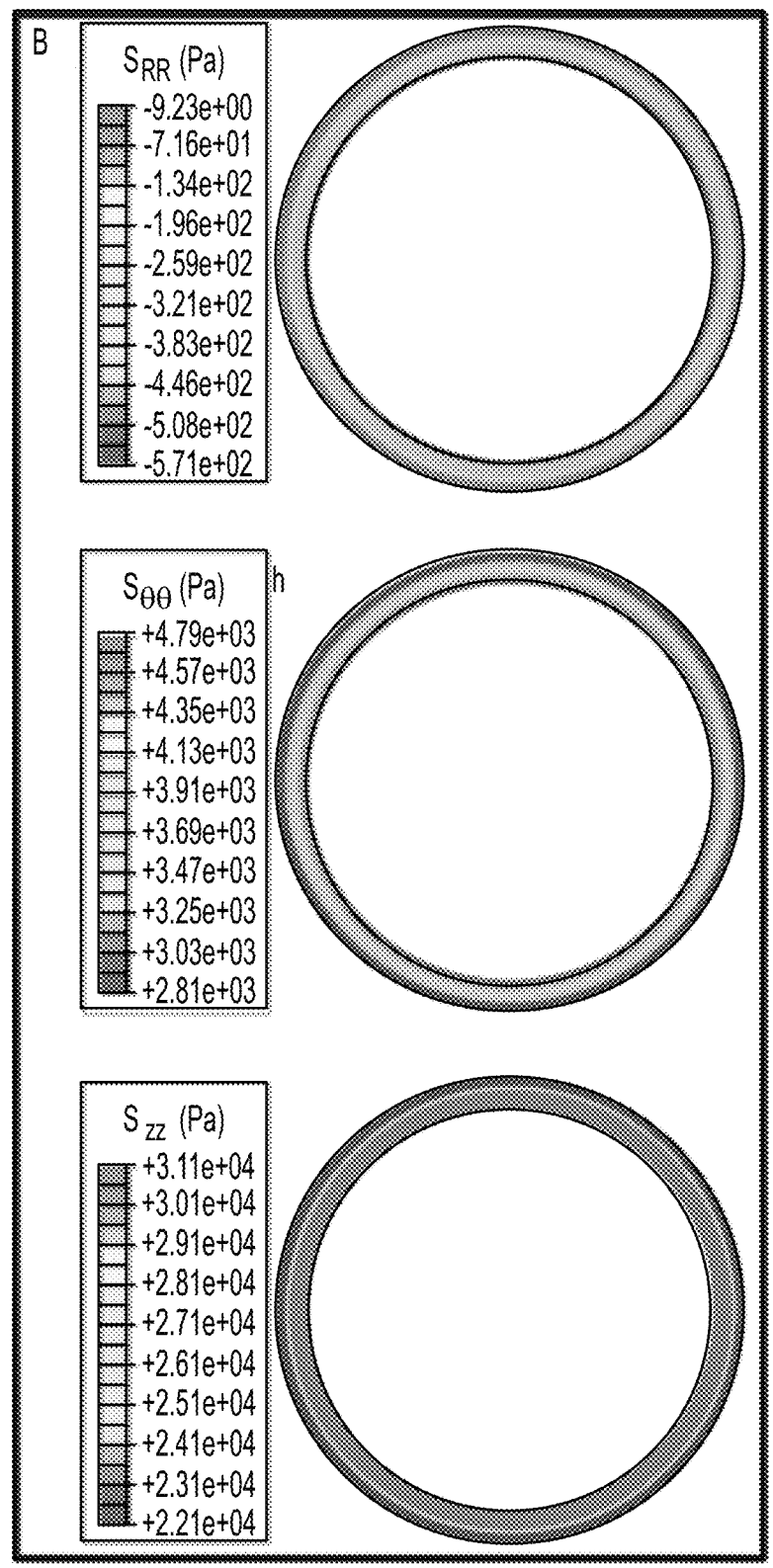
Figure 9C:
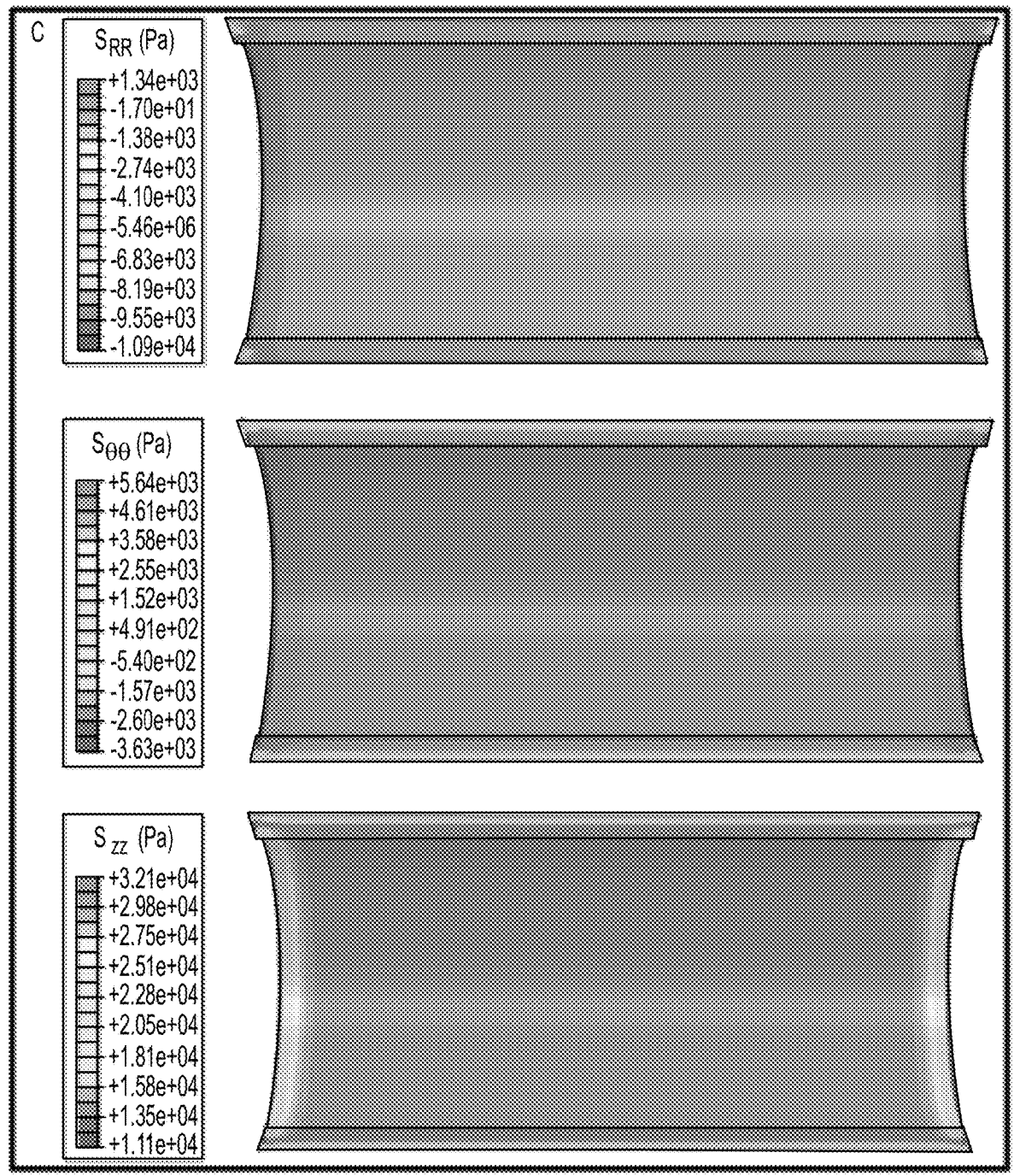
Figure 10:
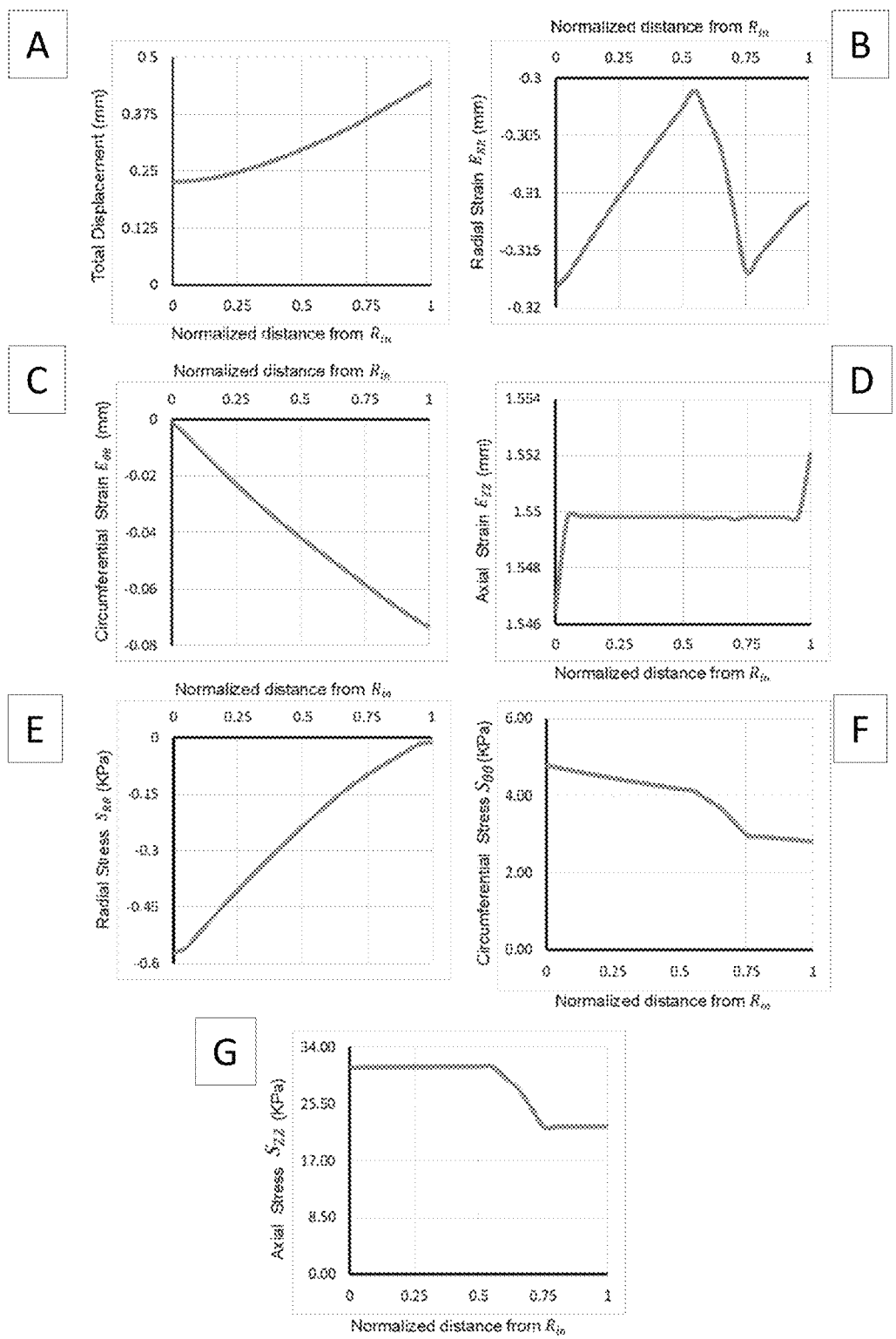
FIG. 10 shows displacement, strain and stress in different directions across the thickness of intestinal wall calculated from computational model results. (A) presents total displacement vs. normalized distance. (B) presents radial strain vs. normalized distance. (C) presents circumferential strain vs. normalized distance. (D) presents axial strain vs. normalized distance. (E) presents radial stress vs. normalized distance. (F) presents circumferential stress vs. normalized distance. (G) presents axial stress vs. normalized distance.

In each model, constants C and D for each layer were calculated using the results of mechanical testing. As the force is applied in the axial direction, tissue initially shrinks in radial direction and becomes thinner due to the negative stress experienced by tissues in the radial direction and positive stress in the axial and circumferential directions (FIG. 9B, 10). An increasing stress pattern was observed for $S_{\theta\theta}$ and $S_{ZZ}$ from the inner to the outer intestinal wall. This stress pattern was decreasing for the radial stress $S_{RR}$ (FIG. 9B, 10). No significant change in stress was observed axially along the length of the intestine except for the ends where the mechanical forces were applied (FIG. 9C, 10).

Total tissue displacement increased from the inner to the outer intestinal wall. Strain components had different behaviors: $E_{RR}$ had negative value for all values across the thickness and decreased in the mucosa and muscularis propria but increased in the submucosa. Circumferential strain, $E_{\theta\theta}$, was negative and decreased across the thickness, whereas axial strain, $E_{ZZ}$, was positive and increased across the thickness (FIG. 10).

Figure 11:
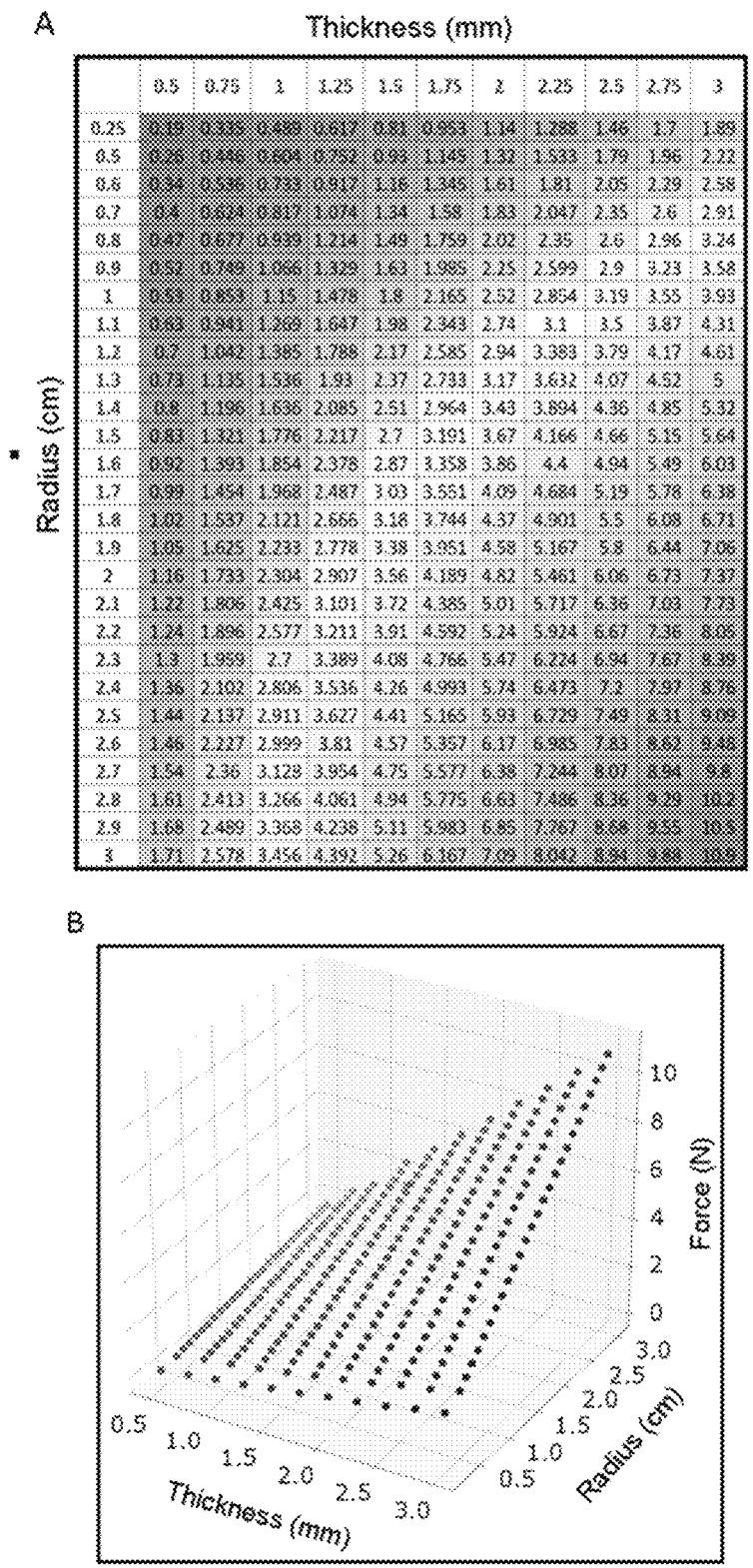
FIG. 11 shows predicted required mechanical force (B) for different geometrical metrics (radius and thickness, A) of small intestine for human subjects.

Having an understanding of the required force for each patient is optimal for lengthening efficiency, without applying excessive mechanical force that may damage the intestinal tissue. As such, computational models were developed covering a combination of varying wall thicknesses and intestinal radii to predict the magnitude of the mechanical forces needed to double the intestinal length. The range of thickness and radius in the developed models were 0.5-3 mm and 0.25-3 cm, respectively. The predicted forces ranged from 0.19 N for (t=0.5 mm, $R_{in}$=0.25 cm) to 10.9 N for (t=3 mm, $R_{in}$=3 cm) (FIG. 11). The magnitude of the predicted required force increased with respect to increasing thickness and radius.

The above examples and embodiments are included for illustrative purposes only and are not intended to limit the scope of the disclosure. Many variations to those methods, systems, kits, and devices described above are possible.

Since modifications and variations to the examples described above will be apparent to those of skill in this art, it is intended that this invention be limited only by the scope of the appended claims. All publications and references cited herein are expressly incorporated herein by reference in their entirety and/or for the specific reason for which they are cited herein.

The invention claimed is:

1. A method of selecting or making an expandable implant for lengthening a segment of an elongate tubular organ in a subject, comprising:
   determining at least two parameters related to the elongate tubular organ of the subject at a target location, wherein the at least two parameters are the radius of the elongate tubular organ of the subject at the target location and the wall thickness of the elongate tubular organ at the target location;
   determining a target amount of force capable of lengthening the elongate tubular organ at the target location using the at least two parameters; and
   selecting or making the expandable implant having one or more characteristics capable of producing the target amount of force.

2. The method of claim 1, further comprising implanting the selected or made expandable implant into the target location of the elongate tubular organ.

3. The method of claim 2, wherein the expandable implant has a proximal end, a distal end, an expanded configuration, and a compressed configuration, and wherein the implanting comprises forming a plication in the elongate tubular organ adjacent to the proximal end and the distal end of the expandable implant when implanted into the elongate tubular organ at the target location in the compressed configuration.

4. The method of claim 1, wherein the expandable implant comprises a self-expanding spring.

5. The method of claim 4, wherein an uncompressed spring length ranges from 5 cm to 8 cm.

6. The method of claim 1, wherein the target amount of force ranges from 0.3 N to 0.8 N.

7. The method of claim 1, wherein two or more expandable implants are selected or made, the method comprising:
   determining the at least two parameters related to the elongate tubular organ of the subject, wherein the parameter is selected from one or more of weight of the subject, height of the subject, age of the subject, a radius of the elongate tubular organ of the subject at the two or more target locations, a diameter of the elongate tubular organ at the two or more target locations, and a wall thickness of the elongate tubular organ at the two or more target locations;
   determining the target amount of force capable of lengthening the elongate tubular organ at the two or more target locations; and
   selecting or making the two or more expandable implants, each having one or more characteristics capable of producing the target amount of force.

8. The method of claim 7, further comprising implanting the two or more expandable implants at a respective one of the two or more target locations.

* * * * *